US007666355B2

(12) United States Patent
Alavie et al.

(10) Patent No.: US 7,666,355 B2
(45) Date of Patent: Feb. 23, 2010

(54) AUTOMATED ANALYZER

(76) Inventors: Tino Alavie, 12 Doncrest Drive, Thornhill (CA) L3T 2T1; Keith Beckley, 400 Warren Rd., King City (CA) L7B 1C4; Andrew Hudson, 128 Yarmouth Road, Toronto (CA) M6G 1X2; Stephen W. Leonard, 80 Lichfield Rd., Unionville (CA) L3R 0W9; Robert Maaskant, 1 Manitou Drive, King City (CA) L7B 1E7; Samad Talebpour, 220 Taylor Mills Dr. N, Richmond Hill (CA) L4C 2T7; William Yang, 119 Mintwood Dr., Toronto (CA) M2M 3A6

( * ) Notice: Subject to any disclaimer, the term of this patent is extended or adjusted under 35 U.S.C. 154(b) by 721 days.

(21) Appl. No.: 11/369,204

(22) Filed: Mar. 7, 2006

(65) Prior Publication Data

US 2006/0210435 A1 Sep. 21, 2006

Related U.S. Application Data

(60) Provisional application No. 60/658,570, filed on Mar. 7, 2005.

(51) Int. Cl.
*G01N 21/00* (2006.01)
(52) U.S. Cl. .................... 422/65; 422/99; 422/100; 422/72; 436/180; 436/43; 436/45; 436/47; 435/288.3; 435/288.7
(58) Field of Classification Search .................... 422/65, 422/72, 99–100; 436/43, 45, 47, 180; 435/288.3, 435/288.7
See application file for complete search history.

(56) References Cited

U.S. PATENT DOCUMENTS

| 5,104,621 | A | 4/1992 | Pfost |
| 5,122,342 | A | 6/1992 | McCulloch |
| 5,206,568 | A | 4/1993 | Bjoernson |
| 5,424,212 | A | 6/1995 | Pinsl-Ober ............... 436/50 |
| 5,620,898 | A | 4/1997 | Yaremko et al. ............ 436/45 |
| 5,650,122 | A | 7/1997 | Harris |
| 5,885,529 | A | 3/1999 | Babson |
| 5,885,530 | A | 3/1999 | Babson |

(Continued)

OTHER PUBLICATIONS

Little et al., "Recent Advances in Robotic Automation of Microplate Assays", Laboratory Automation & Information Management, Elsevier Sci. Publishers BV, Amsterdam, NL, vol. 26, No. 2, Nov. 1, 1994, pp. 89-99.

*Primary Examiner*—Jill Warden
*Assistant Examiner*—Jyoti Nagpaul
(74) *Attorney, Agent, or Firm*—Lynn C. Schumacher; Hill & Schumacher

(57) ABSTRACT

The present invention provides a bar-code driven, completely automated, microplate-based analyzer system for performing chemical, biochemical or biological assays. The analyzer is a modular, bench-top instrument that compactly integrates subsystems for sample dispensing, liquid handling, microplate transport, thermal incubation, vortexing, solid phase separation and optical reading. An internal processor is included for automating the instrument, and a user interface to facilitate communication with the operator via a touch-sensitive liquid-crystal display (LCD), and communicating with a remote network via multiple protocols. The analyzer includes firmware resident within the processing system and the user interface allows the operator to select pre-defined assay batch protocols and the user interface is configured in such as way so as to restrict an operator from programming the firmware.

51 Claims, 35 Drawing Sheets

U.S. PATENT DOCUMENTS

| | | |
|---|---|---|
| 6,042,786 A | 3/2000 | Oonuma |
| 6,326,147 B1 | 12/2001 | Oldham |
| 6,649,182 B2 | 11/2003 | Hsieh |
| 2001/0048899 A1 | 12/2001 | Marquiss |
| 2002/0006362 A1 | 1/2002 | Ohta |
| 2002/0146346 A1 | 10/2002 | Konecke |
| 2003/0170881 A1 | 9/2003 | Davis |
| 2003/0180815 A1 | 9/2003 | Rawson |
| 2004/0202577 A1 | 10/2004 | McNeil |

AUTOMATED ANALYZER

CROSS REFERENCE TO RELATED U.S. APPLICATIONS

This patent application relates to, and claims the priority benefit from, U.S. Provisional Patent Application Ser. No. 60/658,570 filed on Mar. 7, 2005, in English, entitled AUTOMATED ANALYZER, and which is incorporated herein by reference in its entirety.

FIELD OF THE INVENTION

The present invention is related to an automated analyzer particularly for clinical applications.

BACKGROUND OF THE INVENTION

Automated clinical analyzers have recently enjoyed widespread use by diagnostic laboratories for the rapid and reliable detection of analytes in a variety of biological samples. Analyzers are routinely used to perform a wide variety of assays, most of which involve immunoassays where the high affinity and selectivity of an antibody for its antigen is exploited.

Most of the recent efforts of the diagnostic community have focused on the development of products for either high-throughput clinical laboratories or single-use "point-of-care" settings. High throughout screening (HTS) is a mature area of diagnostics that is generally served by large, expensive and complex analyzers. Analyzers with very high throughput capabilities are usually modular in form, with each separate module performing a single step of the assay. For example, modules commonly exist for fluid handling, incubating, vortexing, transport, and reading and analyzing the assay result. The modules are then robotically interconnected to provide full automation. Alternatively, some HTS analyzers are designed as a single unit, with multiple subsystems integrated into a common instrument. Such analyzers are more compact than their modular counterparts and usually have a somewhat reduced throughput, but still require a significant amount of laboratory space.

U.S. Pat. No. 6,042,786 discloses one such system, in which a single pipette in linear motion is used to aspirate and dispense samples and reagents. This system has a throughput of approximately 200 samples per hour and includes on-board reagent storage and refrigeration. In U.S. Pat. No. 5,885,530, an immuno-analyzer is disclosed that fully automates the handling and analysis of a bead-based heterogeneous assay system. This complex system features a centrifugal bead wash station and a re-usable sample dilution well. It is favored for clinical settings in which a high throughput of heterogeneous assays is required. In another instance of the prior art, U.S. Pat. No. 6,649,182 describes an analyzer for use with a biochip that is deposited with an array of receptors for different analytes. This system is useful for screening a large number of samples for the presence of very high number of analytes.

At the other end of the diagnostic spectrum lies point-of-care testing, in which simple, disposable cartridges are commonly used to perform a rapid screening assay. These devices are designed primarily for "doctor's office" or "bedside" applications in which a very low throughput of samples is encountered. Point-of-care screening has traditionally been performed using disposable lateral-flow assay devices. A lateral-flow assay device typically contains a sample pad, a conjugate pad, a membrane with reagent lines and an absorptive pad. The sample is added to the sample pad and flows through the conjugate pad, where it interacts with analyte-specific labeled antibodies, forming a bound complex. The bound complex then flows through a porous membrane to one or more reagent lines, at which point the bound complex and unbound analyte binds. The presence of a coloured line at the reagent indicates a positive result. The sample continues to flow through the membrane to the absorbent pad, where it is absorbed. It is commonplace for a second control reagent line to be added to confirm the event of a positive result. Such a device is used in U.S. Pat. Publication No. 2002/0146346A1, where a single lateral flow platform is used to screen for a panel of several drugs of abuse. Such devices are useful for qualitative analysis, but are generally not useful for obtaining reliable quantitative results.

Recently, the field of point-of-care diagnostics has evolved beyond simple qualitative devices to quantitative or semi-quantitative analyzers that accept single-use, disposable sample cartridges. Most of these analyzers rely on cartridges with advanced internal sample processing capabilities, including sample delivery, reagent delivery, washing, incubation and the absorbance of waste fluids. Microfluidic technologies are often employed to achieve these functions, with capillary action or centrifugal forces used to provide metered fluid delivery. Alternatively, capillaries can be used as valve stops, beyond which fluid flow is only made possible following the application of sufficient air pressure from by an external means.

An example of such a cartridge is provided by U.S. Pat. Publication No. 2003/0170881A1, in which a disposable cartridge for point-of-care settings is disclosed. The cartridge is placed by the operator in the analyzer, which performs an enzyme-based immunoassay for a given analyte. Upon completion of the assay, results are read via electrical means, such as the amperometric or potentiometric reading of thin films, which advantageously reduces the design complexity, size and cost of the analyzer.

Another suitable cartridge for point-of-care diagnostics is described in U.S. Pat. Publication. No. 2003/0180815, in which a simple and disposable lateral flow assay device is adapted for use in an analyzer. Unlike conventional colourimetric lateral flow assay devices, this invention uses an enzyme for the dissolution of a polymer membrane coating an electrode, providing an electrical measurement of the assay result. The cartridges can therefore be inserted into a simple reader that employs a capacitive measurement for the determination of assay results.

Despite the advances made in serving HTS markets and "point-of-care" settings, the needs of small clinics with low-to-moderate throughput requirements have been largely overlooked. An excellent example of these clinics is the so-called "point-of-collection" clinic, in which client or patient samples are routinely collected for analysis. Examples of such medical clinics include cancer, fertility and cardiac clinics and also therapeutic treatment clinics including methadone maintenance clinics and pain management clinics. Another example of a point-of-collection setting is workplace drug testing performed by a large employer on a routine basis. Other examples of small clinics include specialized non-medical laboratories such as food testing or environmental testing laboratories, where periodic sample collection is routinely employed as a safety measure.

In its most efficient form, on-site testing enables a small clinic to obtain test results within minutes. In the case of medical point-of-collection clinics, the rapid availability of the results reduces the costs of testing and allows the physician to provide a much higher standard of care, responding immediately to changes in the patient's condition. On-site testing also assists small non-medical laboratories to enable rapid testing and offers the ability to easily customize and vary the assay test plan.

The needs of smaller sized clinics are therefore likely to be best met by an inexpensive analyzer that is easy to operate. A step towards this goal has been taken in the prior art by the development of microplate-based automated analyzer systems. Such analyzers employ an array of microwells to perform the assay reaction on a per-assay and per-sample basis.

Microplates for such a use are commercially available in a number for formats, the most commonly used format at present being the 96-well 8×12 microplate. Other popular microplate formats provide much more wells are the 384 and 1538-well microplates. For all of such microplates, the many of the physical dimensions are required to meet an industry standard that promotes the usage of a single format across a wide range of analyzer and instruments.

Although microplate-based liquid handling systems and single-function microplate systems such as microplate washers, incubators, agitators and readers are well known in the prior art, only a few examples of compact fully-automated microplate analyzers have been disclosed. One example of a microplate-based analyzer system is provided by U.S. Pat. No. 5,104,621 issued to Pfost et al., where an automated analyzer employing microplates for the purpose of conducting ELISA assays is disclosed. The analyzer employs a number of integrated subsystems to provide a versatile laboratory instrument for the automation and control of assays. Reagents are dispensed from a bulk dispenser into the wells of a microplate. The microplate, reagents and consumables are all housed in a common two-dimensional plane.

Another analyzer that uses a more complex spatial layout of subsystems is disclosed in U.S. Pat. No. 5,122,342 issued to P. F. McCulloch et al., where a magazine containing a plurality of assay-specific microplates is housed within the analyzer. Samples are loaded into the analyzer and are identified by a machine-readable barcode. The analyzer is programmed by the operator to perform a series of assays on a set of samples, and assay reactions are performed in a microplate format, with a different microplate for each assay. Reagents are dispensed from a bulk internal storage apparatus via multichannel plungers. A key aspect of this patent is that the identity of the individual microplate carriers is confirmed while moving the microplate to a given subsystem by reading an identifying barcode affixed to each assay-specific plate carrier.

In another example of microplate analyzers in the prior art, U.S. Pat. No. 5,650,122 provides an automated system for performing an enzyme-linked immunosorbent assay (ELISA). The analyzer automates the processing of two ELISA-based microplates, incorporating sample pipetting, incubation, washing and optical absorbance reading into a single instrument. Although the sample is directly pipetted (and diluted, if necessary) by the analyzer into the microplate, the placement of the sample test tubes is done by the operator and is susceptible to transcription errors. Such an analyzer requires a high degree of skill by a trained operator for proper quantitative analysis.

A fourth microplate-based analyzer system is described in US Patent Application 2002/0006362 A1 (Ohta et al.). This microplate-based analyzer system improves over the prior art by providing a more compact and efficient system. As in the aforementioned microplate-based analyzers, this system employs bulk reagent storage and a liquid transfer station for dispensing reagents from bottles to microplate wells where the assay reaction occurs.

A fifth microplate-based analyzer is commercially available from BMG as the NOVOstar system, which is a compact analyzer system that allows the operator to load both a reagent and a measurement microplate, the latter containing pre-dispensed sample. An internal pipetting system enables the transfer of reagents from the reagent microplate to the reaction microplate, where the assay reaction is initiated. The system further includes means for agitation, incubation, microplate washing, dispensing of additional stored bulk reagents, and optical detection. The analyzer is sold as a fully automated tool for research laboratories.

Unfortunately, none of the four aforementioned microplate-based analyzer systems are designed for use in a small clinical setting. The analyzers all assume a high degree of operator skill, especially for providing such functions as the programming of assay protocols, inventory management of internally-housed reagents, frequent maintenance, and the correct placement of samples within the analyzer. Such requirements represent a large drawback for use in a small clinical setting, where speed and simplicity are crucial.

As mentioned above, a critical requirement for most small clinics is the ability for unskilled personnel such as secretaries or nurses to operate diagnostic analyzers for on-site testing with minimal training. Small clinics often cannot afford the added expense of employing skilled technicians to run a clinical laboratory. Furthermore, there may be regulatory issues that preclude the employment of trained staff in small clinics. This requirement has important consequences for the handling of samples for analysis. Provisions must be made in the analyzer (and cartridge if one is used) to protect against sample transcription errors, which can lead to erroneous results and liability concerns. Equally important is the need for the design of the analyzer to minimize the possibility of unskilled personnel being exposed to potentially hazardous samples.

Due to the lack of analyzers designed specifically for small clinics, clinicians are often forced to choose between using high-throughput analyzers or single-use, point-of-care devices for on-site testing. Unfortunately, the high purchase cost and need for skilled technicians makes HTS analyzers inappropriate and unaffordable for most small clinical settings. Also, as previously discussed, HTS analyzers typically enable sample throughput in excess of several hundred samples per hour, which is far beyond the requirements of small clinics and laboratories. The usefulness of point-of-care diagnostic devices in small clinics is also limited. Although simple disposable devices such as lateral flow assays are useful in very low-throughput applications where a qualitative result is desired, they fail to provide the necessary accuracy for the majority of small clinics that require a quantitative result.

The role of the operator in interpreting the assay result is also problematic in many clinical settings. In addition, manual devices do not automatically provide an electronic record of the test result that can be remotely achieved on a computer system. Although point-of-care analyzers surmount many of these problems, their throughput and need for frequent loading and unloading of the instrument make them impractical for small clinics or laboratories with moderate sample throughput. Unfortunately, many of the cartridges used in such instruments lack the assay diversity needed to perform a wide range of tests. The use of a sample cartridge often prohibits sample dilution, which may be necessary for some assays.

Point-of-care analyzers also often suffer from poor assay repeatability due to poor tolerances in the manufacture of cartridge parameters or insufficient accuracy when dispensing fluids. The repeatability is often further compromised by the lack of sufficient calibrators or controls. This poor repeatability leads to a significantly larger coefficient of variation in the assay result, which limits the dynamic range and precision of the assay. Perhaps most importantly, the use of complex, proprietary, single-sample, single-test disposable cartridges dramatically increases the cost per test relative to that of high-throughput analyzers, squeezing profit margins and increasing the cost of healthcare.

The aforementioned limitations of diagnostic devices have forced many small clinics and laboratories to abandon on-site testing in favour of testing in a centralized laboratory. A centralized laboratory typically uses HTS analyzers to perform tests on samples culled from a number of smaller clinics. This process is costly and time consuming, as it necessitates the shipping of samples from the clinic to the centralized laboratory. Although an individual test may only take minutes to complete by the analyzer in the laboratory, the time interval between shipping the sample and receiving the report can be days. To make matters worse, the assays performed on the large analyzers are usually only semi-quantitative tests that are susceptible to problems associated with matrix effects, sample adulteration and poor specificity. These problems commonly lead to the reporting of false positive results, in which case it is often necessary to perform further quantitative confirmatory testing, leading to further costs and delays.

There is therefore a need for a diagnostic analyzer that bridges the existing gap between HTS and point-of-care analyzers, providing an analyzer that offers moderate throughput, ease of use by unskilled workers, minimal sample handling, low consumable cost and assay versatility in a compact and inexpensive instrument.

SUMMARY OF THE INVENTION

The present invention addresses the need for a moderate-throughput analyzer that does not require skilled laboratory personnel by providing a microplate-based analyzer with minimal operator involvement and decision-making.

In particular, the analyzer solves the problems associated with reagent storage and handling by removing the requirement for internal reagent storage. This is achieved by providing a means for processing sealed and labeled reagent microplates that are easily loaded by an unskilled operator. The pre-filled microplates may contain reagents, standards, or a mixture of both in order to facilitate the automation of one or more assays in a batch format. In a preferred embodiment, a means of punching sealed microwells is provided within the analyzer. Alternatively, the sealed microwells can be punched with an external punch tool prior to being loaded in the analyzer.

Microplates and assay consumables are loaded into the analyzer by one or more carrier trays, which perform the dual role of securing the microplates and assay consumables and also providing a means of transporting the microplates and assay consumable within the analyzer. The means of transportation further includes a transport arm that engages with mechanical features on the carrier trays and transports the carrier trays to various systems and stations internal to the analyzer.

Samples are loaded into a sample housing within the analyzer, where machine readable labels on the sample containers are read. In a preferred embodiment, the machine readable labels also include a list of assays to be performed by the analyzer, which further reduces the role of the operator and thereby the likelihood of human error. In another preferred embodiment, the labels on the microplates and assay consumables are also machine readable. This provides a means for confirming the correct loading of microplates and assay consumables, and also allows for the passage of important information to the analyzer without the involvement of the operator. Such information may include the microplate type, microplate vendor, expiry date, production date, lot or batch number, serial number, reagent or standard identity and location, and reagent or standard concentration.

The analyzer also improves upon the prior art by incorporating one or more pre-programmed assay batch protocols in the analyzer firmware. The firmware, which is preferably restricted from modification by an operator, includes the sequence and timing required for the automation of one or more assays. The firmware may be field-upgraded for the purpose of adding, removing, or modifying assay batch protocols.

The automation of assays is achieved by a microprocessor control means, which directs a series of internal systems and stations to perform all tasks necessary to conduct one or more assays specified in a given batch protocol. The internal systems and stations include an agitation means, a liquid dispensing station for the dispensing of samples, reagents and standards, a thermal incubator, and an optical detection station. The operator interacts with the analyzer via a user interface, which is preferably a touchscreen liquid-crystal display integrated into the analyzer.

The present invention therefore provides an automated analyzer for performing chemical, biochemical or biological assays in a microplate format, comprising;

a plurality of discrete carrier trays for holding and transporting microplates and other assay consumables, where said microplates and assay consumables have a uniquely identifiable label, and where microplates with microwells containing a reagent or standard are initially provided in a sealed format;

means of presenting said carrier trays to an operator for the purpose of loading or unloading said microplates and other assay consumables;

a plurality of carrier tray supports within said analyzer for holding said carrier trays in particular locations;

a carrier tray transport means for transporting said carrier trays as required within said analyzer;

a sample housing for holding one or more sample containers, where each sample container has a uniquely identifiable machine readable label;

reading means for reading a machine readable label;

piercing means for piercing said sealed microwells for allowing access to the reagents or standards within the microwells;

a liquid dispensing system for transferring a sample to said microwell and for transferring one or more of said reagent or standard to one microplate from another microplate;

agitation means for agitating one or more microplates;

a thermal incubator for thermally incubating contents of said microwells of one or more microplates;

an optical detection station including an optical detection system for measuring an assay signal from one or more microwells;

a user interface enabling interaction between the analyzer and an operator;

microprocessor control means including firmware pre-programmed with one more batch protocols, wherein said batch protocols describe all steps required for the automation of one or more assays performed on one or more samples; and a means for field-updating said firmware for the purpose of adding, removing or modifying batch protocols.

As described above, the assay firmware includes pre-programmed assay batch protocols that provide the sequence and timing required for the automation of one or more assays. A batch protocol run that performs one or more assays on a set of samples is initiated as follows. The analyzer first scans the barcodes of samples loaded into the analyzer and determines the list of all assays required by the set of samples. The list of assays to be run on a particular sample can either be contained within the machine-readable sample labels, or can be manually entered by the user on a per-sample basis. The analyzer then cross-references the list of all assays with the sample batch protocols residing in the analyzer firmware. The subset of compatible sample batch protocols is then presented to the operator, who is instructed to select a preferred sample batch protocol. The analyzer then instructs the operator to load the analyzer with the microplates and assay consumables required for the chosen sample batch protocol. The sample batch protocol is then performed by the analyzer, whereby assay signals are obtained for each assay performed on each sample. Pre-determined dose-response curves for each assay are then employed to determine the analyte concentrations within the samples.

The present invention therefore also provides a method of automating chemical, biochemical or biological assays in a microplate-based automated analyzer, comprising the steps of;

instructing an operator to insert one or more sample containers into an analyzer, where each sample container contains a sample and has a uniquely identifiable machine readable label;

obtaining a list of assays to be performed on each sample by an assay list input means;

compiling a list of all assays to be performed on said samples;

cross-referencing said list of all assays with a set of sample batch protocols residing within firmware of said analyzer to determine a subset of sample batch protocols that can be employed to perform said list of assays, wherein said sample batch protocols describe the sequence and timing of all actions required to perform one or more assays on one or more samples, and wherein said sample batch protocols are pre-programmed into the firmware of said analyzer;

instructing said operator to select a sample batch protocol from said subset of sample batch protocols;

instructing said operator to load microplates and other assay consumables required by said selected sample batch protocol, where said microplates and assay consumables have a uniquely identifiable label, and where microplates with microwells containing a reagent or standard are initially provided in a sealed format;

performing said selected sample batch protocol; and determining one or more analyte concentrations for each sample, wherein said analyte concentrations are obtained using assay signals measured during automation of said sample batch protocol and dose-response curves for assays performed by said sample batch protocol, and wherein said dose-response curves are determined by a separate calibration batch protocol and stored within said analyzer.

The automation of a sample batch protocol requires the use of a dose-response curve for each assay performed by the protocol. Such dose-response curves are obtained via a separate calibration batch protocol, whereby standards with known analyte concentrations are measured in the place of samples. In a preferred embodiment, standards are introduced into the analyzer in a microplate format.

A calibration batch protocol run is performed as follows. The analyzer first offers the operator a list of all available batch calibration protocols residing in the analyzer firmware. The operator selects a desired batch calibration protocol and the analyzer instructs the operator to load the analyzer with the microplates and assay consumables required for the chosen calibration batch protocol. The calibration batch protocol is then performed, whereby assay signals for standards with known analyte concentrations are measured for each assay in the batch protocol. The resulting assay signals and known concentrations are mathematically fitted to a known functional form, which generates dose-response curves for each assay. The dose-response curves are stored within the analyzer for use in a future sample batch calibration protocol run. In a preferred embodiment, a companion calibration batch protocol exists for each sample batch protocol within the analyzer firmware.

Therefore, in another aspect of the present invention there is provided a method of calibrating automating chemical, biochemical or biological assays on a microplate-based automated analyzer, comprising the steps of;

providing to an operator a list of calibration batch protocols residing within the firmware of said analyzer, wherein said calibration batch protocols describe the sequence and timing of all actions required to calibrate one or more assays; and wherein said calibration batch protocols are pre-programmed into firmware of said analyzer;

instructing said operator to select a calibration batch protocol from said list of calibration batch protocols;

instructing said operator to load microplates and other assay consumables required by said calibration batch protocol, where said microplates and assay consumables have a uniquely identifiable label, and where microplates with microwells containing a reagent or standard are initially provided in a sealed format;

performing said selected calibration batch protocol; and determining dose-response curves for each assay performed by said calibration batch protocol; wherein said dose-response curves are obtained by fitting measured assay signal and known analyte concentrations to mathematical functions;

storing said dose-response curves within said analyzer for future use by a corresponding sample batch protocol, whereby analyte concentrations in samples are determined.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which.

DETAILED DESCRIPTION OF THE INVENTION

Figure 1:
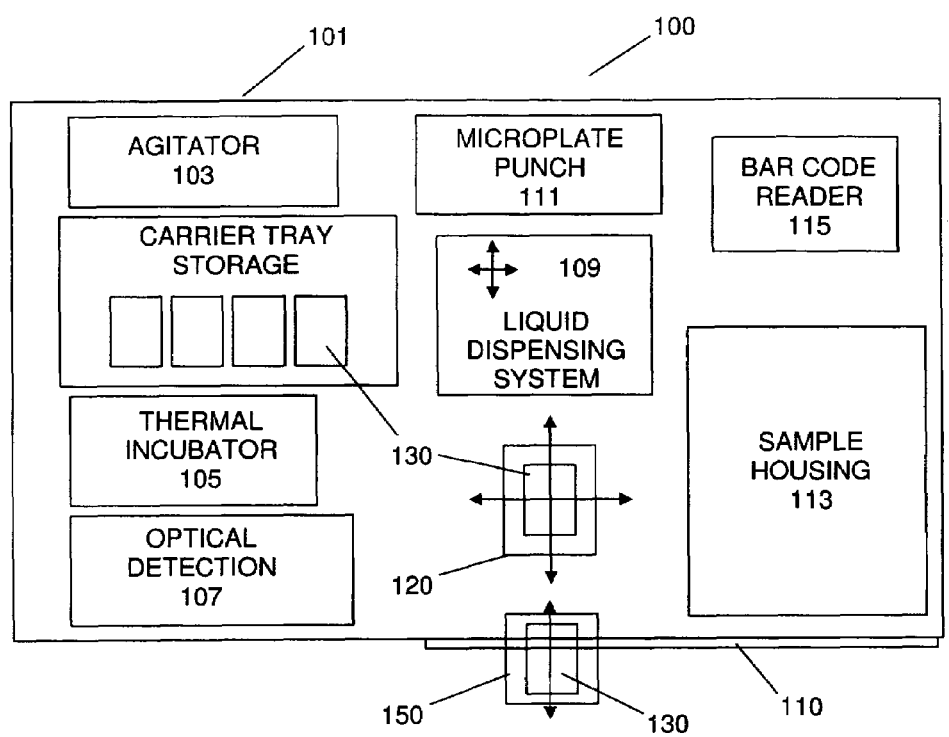
FIG. 1 is a schematic outlining the major subsystems within the analyzer.

The present invention provides a bar-code driven, completely automated, microplate-based analyzer system for performing chemical, biochemical or biological assays. A schematic of a general embodiment of the analyzer system according to the invention is shown in FIG. 1 generally at 100. The analyzer 100 comprises an enclosure 101 with a door 110 for inserting samples, microplates, and other consumables into the system. A plurality of systems and stations reside within the analyzer, including an agitator 103, a thermal incubator 105, an optical detection system 107, a bar-code reader 115, a liquid dispensing system 109, a microplate punch device 111 and a microplate carrier tray transport system 120.

Unlike microplate-based analyzers known in the prior art, the present analyzer does not employ internally-stored bulk reagents. Instead, the analyzer accepts pre-filled, sealed and barcoded reagent microplates with much smaller reagent volumes than traditionally employed in automated analyzer systems. Such reagent microplates were recently described in a co-pending U.S. patent application Ser. No. 11/363,521 entitled "MICROPLATE ASSAY KIT" filed on Feb. 28, 2006, published as U.S Patent Publication No. 2007/0202010.

A microtiter plate, or "microplate" as used hereinafter, is an array of multiple "wells" that are used as small test tubes in which the assay is performed. The microplate has become a standard tool in analytical research and clinical diagnostic testing laboratories. It typically can have 6, 24, 96, 384 or 1536 sample wells arranged in a 2:3 rectangular matrix. Microplates have also been manufactured with 3456 or even 9600 wells. Each well of a microplate typically holds somewhere between a few to a few hundred microliters of liquid. The term "microplate", as used herein, describes both a solid two-dimensional array of microwells, and also a single one-dimensional linear array of microwells (the so-called "stripwell" format), where the stripwell is placed in an appropriate supporting device (such supports are well known in the prior art).

Figure 2:
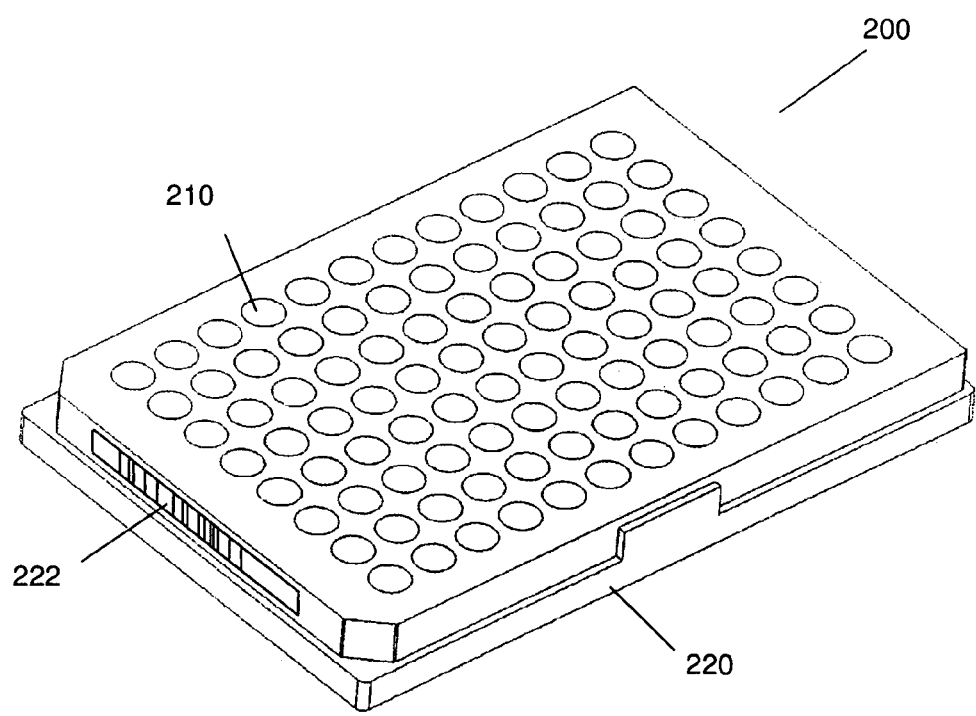
FIG. 2 is a perspective view of a microplate.

FIG. 2 shows an example of such a microplate prior to being sealed. The exemplary microplate 200 preferably adheres to an industry standard discussed above and contains a rectangular array of 96 cylindrical wells 210 and an outer flange 220. Each well has a preferred working volume of approximately 250 microliters. A barcode label 222 applied to the side of the microplate provides information relating to the identity, volume and location of reagents contained within the microwells. The label may further contain additional information such as the batch or lot number of the reagents, the expiry date of the reagents, and details relating to the physical shape, size and vendor of the particular microplate. The microplate 200 is typically made out of polyproplyene, although other materials including glass and polystyrene are also possible. Furthermore, other microplate formats with different well densities including 384-well and 1536-well microplates are also envisioned by the invention as discussed above.

Pre-filled and sealed microplates 200 are loaded into the analyzer though door 110 and onto a carrier tray 130 housed on a carrier tray support 140 located on a loading arm 150. The carrier tray 130 possesses a holding means for supporting microplate 200 in a stable and precise orientation relative to the carrier tray 130. In a preferred embodiment, the loading arm 150 is extendable and retractable in one or more dimensions beyond the analyzer frame 101, through the door 110, for ease of loading microplates onto a carrier tray by the operator. The microplate carrier tray transport system 120, equipped with a carrier tray engaging and disengaging means, is capable of moving a microplate carrier tray 130 from its support 140 on the loading arm 150 to any of the various microplate subsystems within the analyzer. Each subsystem, including the carrier tray storage station, is fitted with a carrier tray support 140 for securing a microplate carrier tray 130. The transport system 120 moves each microplate carrier tray 130 in at least two dimensions.

Also loaded through the door 110 are other microplates to be processed by the analyzer. Each additional microplate is loaded by the operator onto a distinct carrier tray 130 for internal transport. These additional microplates may include supplementary reagent microplates (more than one reagent microplate may be used to perform a set of assays), calibrator or control microplates containing standards to be used when calibrating or verifying assay performance, microplate tip boxes containing arrays of disposable pipette tips to be used by the liquid dispensing system, and reaction microplates. The assay reaction is performed and measured in a reaction microplate, and there are many different physical formats of reaction microplates that may be used in the analyzer 100. For assays in which absorbance in measured, the reaction microplate is preferably made of transparent polystyrene and possess an optically flat bottom. Assays with reporter labels that generate luminescence or fluorescence are preferably measured with black reaction microplates that possess a transparent bottom. The bar code 222 label applied to the side of the microplate can uniquely identifiy the type, vendor and mechanical dimensions of the reaction microplate. Reaction microplates are typically loaded into the analyzer 100 as unsealed and empty microplates, but they may also contain solid phase reagents such as lyophilized antibodies.

All microplates 200 filled with liquids (i.e. reagents or standards) are typically sealed with a metallic foil such as aluminum, but may instead be sealed by other materials such as a transparent plastic film. The microplate seal may be pierced by the operator using a piercing lid known in the prior art, manually peeled, or the microplate seal can be automatically pierced within the analyzer. The latter operation can be performed by distinct punch station 111 as shown in FIG. 1, where a pin or blade is vertically contacted with the upper surface of one or more microwells at a time. Alternatively, the punch may reside within the analyzer 100 as a tool that may be temporarily accessed by another subsystem (such as the liquid handling system or the carrier tray transport system) for punching microwell seals.

Once loaded with operator-supplied microplates, the individual carrier trays 130 are housed within the analyzer 100. The carrier trays 130 may either be stored on or within or on the internal subsystems (i.e. the agitator, thermal incubator and optical detection system) or may be stored in separate fixed carrier tray storage supports. The fixed carrier tray supports can be arranged in number of different spatial formats including a vertical magazine format or alternatively in a planar format. In a preferred embodiment, the fixed carrier trays 130 are arranged with no overlap in the vertical direction (e.g. in a planar format or in a vertically staggered staircase format), which makes multiple carrier trays 130 simultaneously accessible to the liquid dispensing system and enables the rapid transfer of liquids from one microplate 200 to another microplate without requiring the carrier tray transport system to move the individual carrier trays 130.

Alternatively, carrier trays 130 within the analyzer 100 may be housed in a combination of internal subsystems and carrier tray storage supports. In another preferred embodiment, the agitator system 103 and the fixed carrier trays 130 are arranged in such a way as to ensure no vertical overlap, and also an alignment of microplate rows or columns in one horizontal direction. This configuration ensures that multichannel pipetting among all microplates 200, disposable tip changing, and agitation of a microplate 200 located on the agitator 103 can all be achieved without the need for the carrier tray transport system to move any microplates 200.

It should be understood that this embodiment, in which a loading arm 150 is employed to load microplates into the analyzer, is not intended to be limiting in scope but rather serves as an example of one of many loading embodiments. In another simpler embodiment, microplates 200 are loaded directly onto internal microplate carrier trays by the operator through the door 110. In such a case, it is important to recognize that not all plate carriers 130 need to be movable. For example, if the storage location of the plate carrier 130 for a microplate disposable tip box is always directly within range of the liquid dispensing system 109 via translation of the dispensing system, then the plate carrier 130 can remain fixed at all times. In such a case, it may be necessary to provide a dedicated per-fixed-carrier barcode reader or a movable barcode reader that can interrogate barcodes on microplates in fixed carrier trays.

While moving the microplate carrier trays 130 in the analyzer 100, each microplate 200 is scanned by the barcode reader to ascertain pertinent information about the identity, including, but not limited to, microplate type (reaction, reagent, calibrator, pipette tip, etc.), microplate manufacturer and size, reagent identity, reagent volume, reagent location (i.e. microwells within microplate), microplate seal type and microplate seal manufacturer. Although the present general embodiment describes the use of barcodes for sample containers, microplates and consumables, a wide variety of labels are envisioned by the invention for this purpose. These labels include one- and two-dimensional barcodes, simple text that the operator inputs to the analyzer via an interface, machine-readable text and radio frequency bar codes.

In addition to microplates and consumables, sample containers are also loaded via the door 110. Alternatively a separated door may be used for loading samples and disposables used when dispensing samples (e.g. disposable single channel pipette tips). Samples are loaded in pre-barcoded containers that enable the analyzer to determine the requested tests on a per-sample basis with the barcoded containers being placed in the sample housing 113, which may for example be a standard carousel for holding one or more sample containers. Barcodes are read either by a common scanning barcode reader 115 that is also used for reading microplate barcodes, or by a separate barcode reader (not shown) that is dedicated to reading sample container barcodes. In such a case, depending on the spatial arrangement of samples within the sample housing unit, individual barcodes can be read either by scanning or by physically moving the sample containers relative to the barcode reader. As described above, the means of interrogation of sample labels is not intended to be limited to barcodes.

Referring again to FIG. 1, a liquid dispensing system 109 is provided within the analyzer 100 for transferring liquid reagents, calibrators, controls, standards and samples into a microplate well 210. The system 109 may comprise a single robotic pipette or may comprise other liquid handling system configurations, such as a multichannel pipettor for dispensing from one microplate 200 to another and a single channel system for accurately dispensing sample. The liquid dispensing system 109 may employ air displacement, peristaltic, syringe, positive displacement, or other dispensing technologies. The dispensing head may employ disposable tips or may use a single tip that is cleansed in a washing station that is further included within the analyzer. In an embodiment characterized by a multichannel pipettor for microplate to microplate transfer and a single channel pipettor for sample dispensing, the single channel and pipettor is movable in at least two dimensions so that sample can be transferred from a sample container to a microplate well. The sample containers themselves may also be movable in one or more dimensions (or relative to one or more axes) so as to limit the number of dimensions of motion of the single-channel pipettor to two provided that the reaction microplate receiving the samples can be moved in a third orthogonal direction via the carrier tray transport system. Also in this embodiment, the multichannel pipettor is movable in at least one dimension (the vertical dimension). Motion of the multichannel pipettor in two or more dimensions may be preferable to enable the most rapid transfer of liquid between microplates.

The determination of liquid volumes in microplates and sample containers, which may be necessary to manage re-use of microwells containing reagents for more that a single assay, or for the accurate and repeatable pipetting from sample containers with varying volumes, can be achieved via a variety of known methods. The volume of reagents consumed from a particular microwell on a reagent or standards microplate can be tracked by continuously subtracting the volume of aspirated liquid from the initial volume barcoded on the microplate for the microwell. Alternatively, physical means such as capacitive sensing pipettor tips can be employed. For the case of sample pipetting, the volume can either by determined by a physical contact means or alternatively by a non-contact means such as an ultrasonic displacement sensor. Alternatively, the sample volume can be barcoded according to a prior volumetric measurement.

The analyzer 100 also includes thermal incubation station 105 for maintaining the temperature of a microplate 200 at a fixed value for a time interval, which is typically done while an assay reaction is taking place. The incubator 105 is preferably an enclosed housing with a plurality of active heat sources and temperature sensors in order to establish and maintain a prescribed temperature with minimal thermal gradient among microplate wells 210. This can be achieved following any one or many designs known in the prior art. The incubator 105 includes a carrier tray support for receiving a microplate housed on a carrier tray.

In a variation of the present embodiment, the incubation system 105 can be a passive thermal incubator, where the role of the incubator is to provide a constant (but not accurate) thermal profile among the wells of a microplate 200. This is readily achieved by bringing a large thermal mass in close contact with the bottom surface of a microplate. The large thermal mass, unable to support thermal gradients, establishes a sufficient degree of thermal equilibrium among the microplate wells. As described in a pending U.S. patent application entitled "METHOD OF COMPENSATION OF DOSE RESPONSE CURVE OF AN ASSAY FOR SENSITIVTY TO PERTURBING VARIABLES" and filed on Jan. 19, 2006 with Ser. No. 11/334,739, (published as US Patent Publication No. 2006/0177088 which is incorporated herein by reference in its entirety) such a device can be used to accurately perform assays provided that the global variation in temperature is compensated by recalibrating the assay using a signal dependent on temperature.

FIG. 1 also shows agitation system 130 for providing adequate mixing of the reactants within the wells 210 of a microplate 200. The agitator 130 includes a carrier tray support for receiving a microplate 200 housed on a carrier tray 130. A broad range of known agitation means may be used in the analyzer of the present invention, including individually-addressable motorized orthogonal translation stages for providing any type of motion and also orbital motion systems involving circular motion constraints.

The general schematic of the invention according to FIG. 1 further includes an optical signal detection system 107 for the measurement of an assay signal. The detection system 107 may employ any one or more of several known optical detection means, including, but not limited to, absorbance, fluorescence, luminescence, chemi-luminescence, electro-luminescence, time-resolved fluorescence, and fluorescence-polarization. The system 107 may employ a single scanning head for interrogating individual microplate wells 210, or may comprise a scanning multichannel head for measuring a row or column of microwells 210 simultaneously. In other embodiments, the optical system 107 may employ a spatially fixed single or multichannel detection head, whereby individual microwells 210 are scanned by moving the microplate carrier tray 130 relative to the fixed head via the carrier tray transport system 120.

If the optical detection system 107 involves optical radiation being either detected from and/or directed onto the bottom surface of the microplate (which in turn requires that the reaction microplate itself has a transparent bottom surface), the carrier tray 130 for the reaction microplate must be open immediately below each microplate well 200. This can be achieved by a single broad opening below each of the wells 210, or by placing a through hole in the carrier tray 130 on a per-well basis. The latter scheme is advantageous in that it if a sufficiently thick and thermally conductive material is chosen for the carrier tray 130, then the carrier tray can assist in removing unwanted thermal gradients among adjacent microwells during incubation or optical detection. Such a scheme was recently disclosed as an important component of a forced-air photometer system in U.S. Pat. No. 5,307,144 issued to T. Hiroshi et al.

The use of distinct thermal incubation systems 105 and optical detection systems 107, as shown in FIG. 1, is advantageous for certain classes of chemical assays in which the assay signal during optical detection is not significantly sensitive to temperature. Examples of such assays are biochemical assays where a "stop solution" is employed to arrest a reaction prior to detection. However, there are numerous assay types for which the signal is highly sensitive to temperature fluctuations during detection. A prime example of such kinetic assays is the enzyme immunoassay (EIA), where the rate of absorbance change is measured. A preferred embodiment of the analyzer system 100 disclosed herein therefore includes a single combined detection and thermal incubation system (not shown). Incubation and optical detection systems with a closed format and active thermal control are well known in the prior art and are commonly used within laboratory-based optical microplate readers. Alternatively, the incubator can be a passive thermal incubator as described above, which does not require a closed thermal environment. In such a case, either scanning the optical head or translation of the microplate carrier 130 relative to the optical head can be performed openly within the analyzer 100, provided that a sufficiently low level of background light is maintained within the analyzer.

Finally, it may also be preferable for certain types of assays, particularly those involving separation of a solid phase, to add a washing subsystem to the aforementioned embodiment. Washing of a microplate 200 can be achieved via a wash buffer located in a supplementary microplate well or alternatively may be provided internally as a bulk wash buffer at a separate microplate washing station. It is noteworthy that the internal storage of a wash buffer does not depart from the goal of providing a system without the need for assay-specific internal reagent storage, since a wash buffer is generally common among a wide variety of assay formats.

In addition to the systems and stations described above, the analyzer 100 further includes an interface that allows for interaction between the operator and the analyzer. The interface can take many different forms including a remote computer interface or an integrated display and data input device. In a preferred embodiment, the interface is a touchscreen liquid crystal display. Furthermore, the analyzer preferably provides a means for transmitting test results, raw data, system statistics and other useful information to a separate computer system or data network. Preferred embodiments of the transmission means include wireless and Ethernet devices and protocols.

The analyzer 100 further includes a microprocessor-based control system for automating the operation of assay protocols. The analyzer 100 includes firmware pre-programmed with a set of sample batch protocols and calibration batch protocols, where each batch protocol describes the sequence and precise timing of operations needed to perform one or more assays. In addition to providing the assay automation instructions, the batch protocols also include information relating to the types of microplates and consumables that are needed to perform the assays. For each sample batch protocol, there is a corresponding batch calibration protocol. Unlike software that provides an operator with a means of directly configuring batch protocols, as is commonly provided in prior-art microplate analyzers, the assay firmware in the present analyzer 100 is resident within the processing system. In a preferred embodiment, the user interface provides a means for the operator to select pre-defined assay batch protocols but does not provide a means for the user to configure new assay batch protocols. Thus, preferably the user interface is configured in such as way so as to restrict an operator from programming the firmware.

The present automated analyzer 100 further includes a means for field-updating the firmware for the purpose of adding, removing or modifying batch protocols. For example, a new batch protocol can be added to the currently available batch protocols by a field technician using a communications port within said analyzer 100 that is connected to a computer. Such communications ports can include, for example, USB or serial ports. In a preferred example, the analyzer 100 includes an internet connection (e.g. via an Ethernet or a wireless link) that enables a remote firmware upgrade.

Figure 3A:
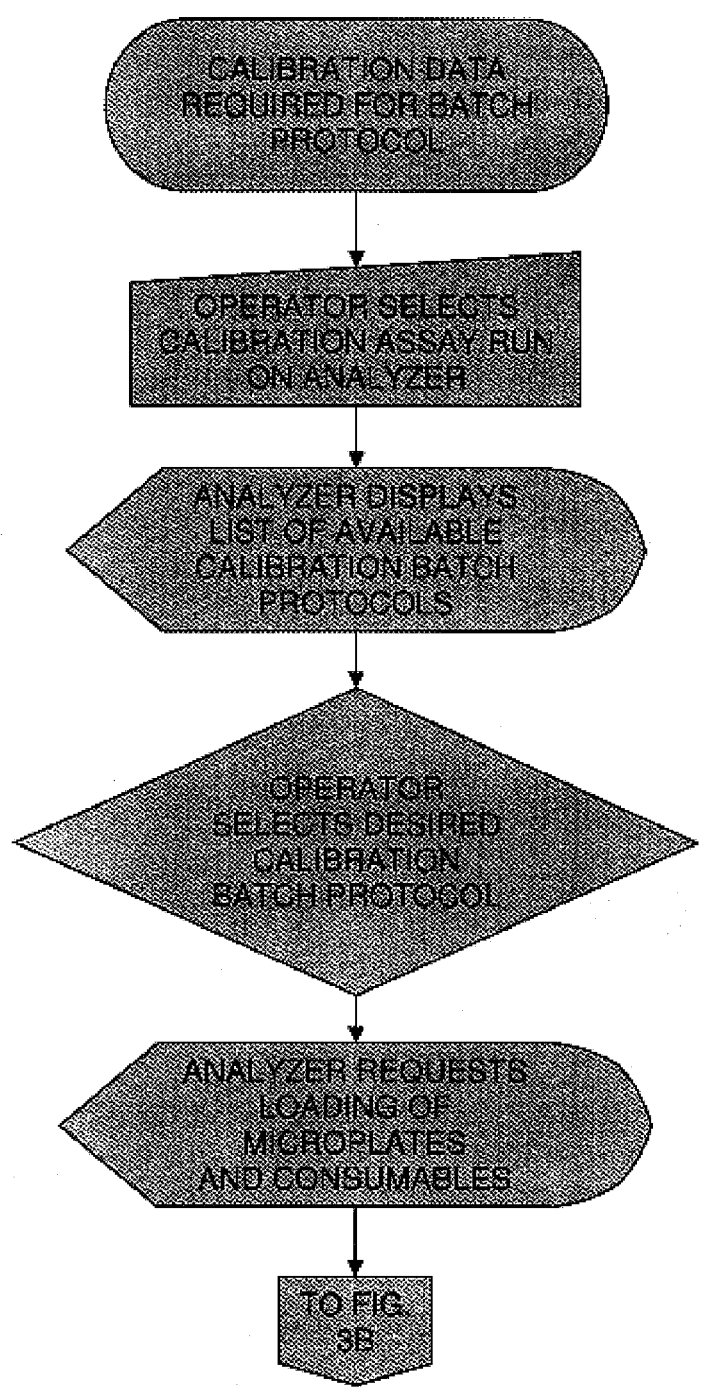
FIG. 3 is a flow chart outlining the primary operational sequence of a calibration batch protocol performed by the analyzer.
Figure 3B:
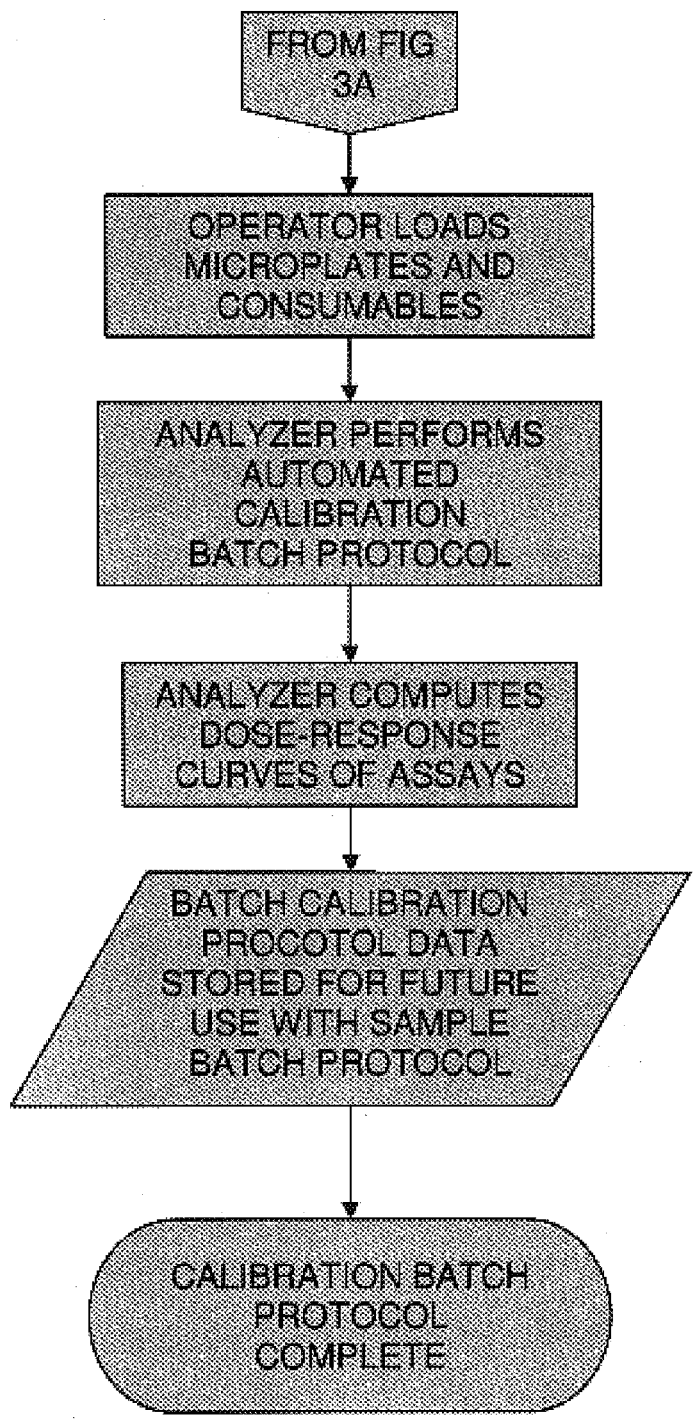

Prior to performing automated assays for the determination of analyte concentrations in samples, it is first necessary to determine a dose-response curve for each assay to be measured. A calibration batch protocol run must therefore be performed prior to performing the corresponding sample batch protocol run on unknown samples. The steps that are taken when performing a batch calibration protocol run are shown schematically in FIG. 3. The calibration batch protocol prescribes calibration assays involving known standards to produce and retain fitted dose-response curves for each assay. Calibration batch protocol runs are initiated by the operator by selecting a calibration run via the analyzer interface. The analyzer 100 then displays a list of available calibration batch protocols that may be run, showing to the operator the appropriate batch protocol name or number. After the operator selects the desired calibration batch protocol, the analyzer 100 will request that the operator load the required microplates and consumables for the run. These consumables may include a reagent microplate, a calibration microplate containing microwells having different concentrations of known standards, a reaction microplate, and disposable pipette tips.

The analyzer then performs the automated batch calibration run and obtains assay signals from standards with known concentrations for each assay in the calibration batch protocol. The signals and concentrations are fitted to known mathematical functions to obtain dose-response curves for each assay, as per the process steps prescribed in the calibration batch protocol programmed within the analyzer. The resulting calibration data is stored within the analyzer so that it can be accessed when performing the corresponding sample batch protocol at a later time. In a preferred embodiment, the calibration batch protocol specifies a time interval over which the fitted dose-response curves are to be employed when analyzing subsequent sample batch protocol runs. After the specified time has elapsed, the operator is directed to initiate a new batch protocol calibration run.

Although the process steps required for obtaining dose-response curves can be programmed in entirety into the analyzer 100 via the calibration batch protocol, it may preferable to supply the analyzer with information regarding the details of the curve fitting methods used to obtain dose-response curves. Such details may include parameters such as initial guess values for curve fitting and error checking parameters to ensure that the curve fitting is accomplished correctly. These details are preferably inputted to the analyzer system 100 via barcodes 222 on the microplates 200 employed by the calibration batch protocol, which allows the manufacturer of reagent microplates to pass such details to the analyzer 100 without the involvement of the operator.

Figure 4A:
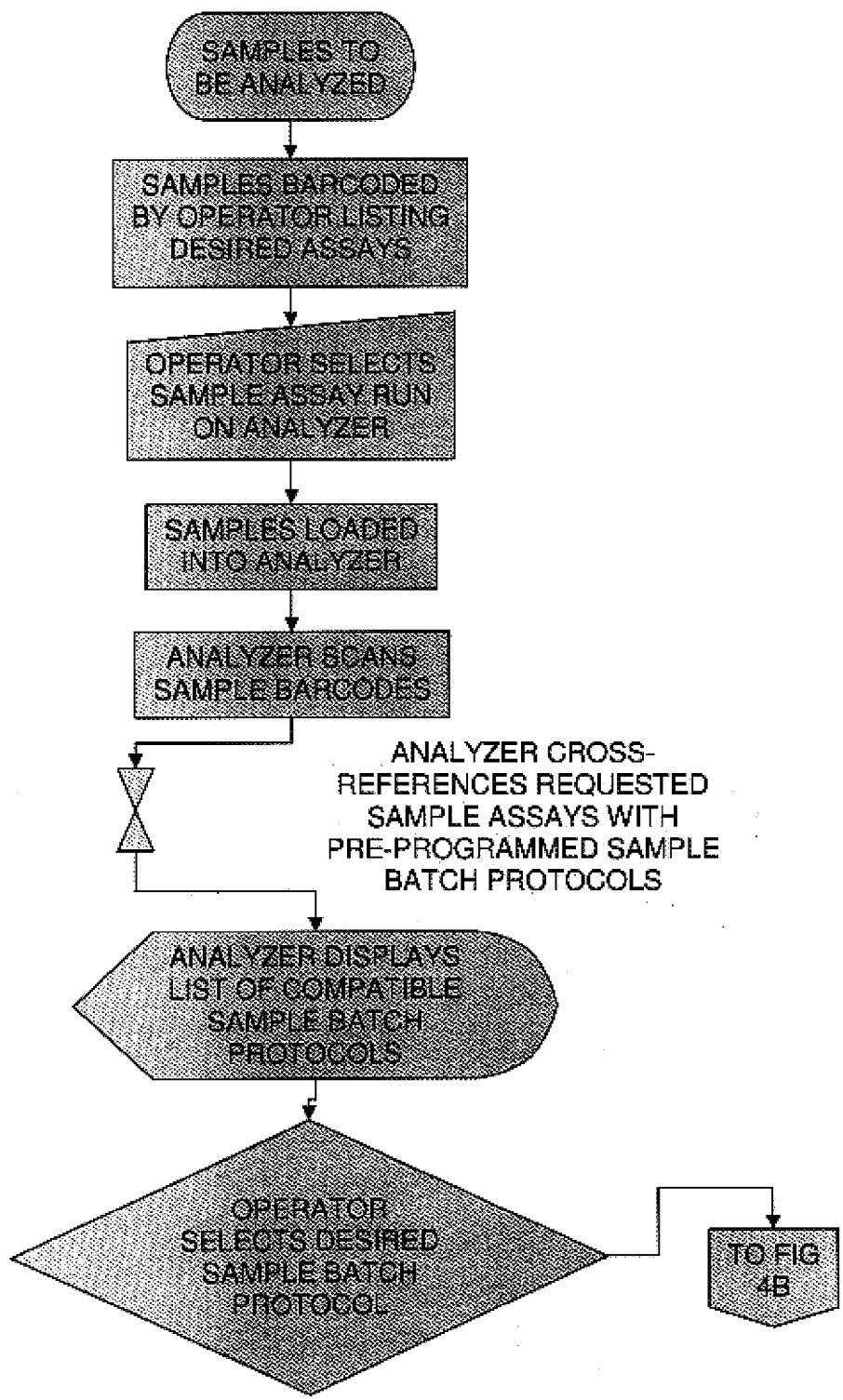
FIG. 4 is a flow chart outlining the primary operational sequence of a sample batch protocol performed by the analyzer.
Figure 4B:
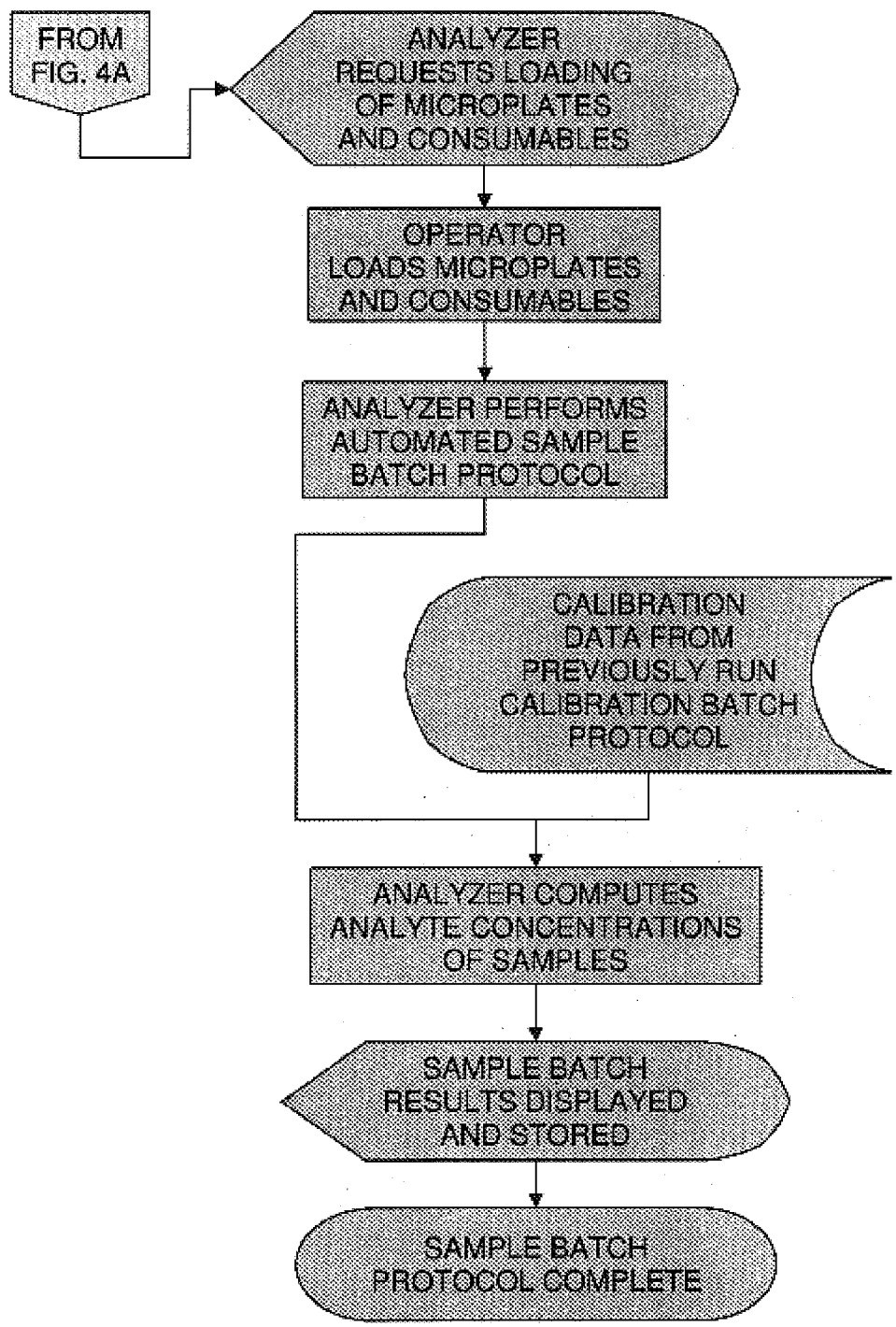

The sequence of steps performed by the analyzer 100 when performing a sample batch protocol run is shown in FIG. 4. The operator first barcodes all samples with information including the sample identity (e.g. a patient name or serial number) and a list of the assays to be performed on the sample. A sample run is then initiated by the operator selecting a sample run on the analyzer interface. The operator is subsequently instructed by the analyzer 100 to load barcoded samples into the analyzer.

The analyzer 100 reads the barcodes of all samples and compiles a list of. all assays to be run by the set of samples. The analyzer 100 then cross-references the list of assays required by all the samples with the set of sample batch protocols stored in the analyzer memory. The names and/or numbers of the different batch protocols compatible with the set of assays required by the samples are then displayed to the operator, who selects the appropriate sample batch protocol. The analyzer 100 then prompts the operator for the required microplates and consumables to perform the selected sample batch protocol, following which the sample batch protocol run is initiated by the analyzer.

The measurement of unknown samples via the analyzer results in a set of assay signals, from which the analyzer 100 must extract the correct analyte concentrations. This is achieved by using the dose-response curves obtained from a previously performed calibration batch protocol run, which are preferably stored within the analyzer memory. The dose-response curves enable the analyzer 100 to back-calculate the analyte concentrations from the assay signals, thus obtaining a determination of the analyte concentration in each sample assayed. These sample results are displayed or transmitted to the operator, completing the sample batch protocol run.

It is also possible to verify the performance of one or more assays that are contained within a given batch protocol by including controls in the sample housing. Such controls are processed identically to samples, and may include multiple analytes, in which case the control barcode would list all assays measuring the multiple analytes. It is furthermore advantageous for the analyzer to automatically make the determination of whether or not the results of the control assays meet the necessary performance criteria. Such criteria is advantageously entered into the analyzer via a direct means that does not involve the operator. In a one embodiment, the performance criteria is provided in the sample batch protocol. In other embodiments, the performance criteria is entered via either the barcode on the control vessel or a microplate barcode. In such embodiments where the analyzer is automatically comparing the control assay results with performance criteria to determine the validity of an assay, the barcode on the control vessel preferably identifies the liquid as a control.

In the preceding description of the sample and calibration batch protocols, the protocols were considered from a general perspective and were not described in detail. Indeed, the present invention anticipates a wide variety of batch and calibration protocols involving different combinations of assays. In one embodiment, the batch protocols involve performing different assays sequentially, whereby samples are processed in parallel on a per-assay basis. In a preferred embodiment, the assays are performed on a microplate column- or row-wise basis so as to enable rapid multichannel dispensing of assay reagents.

A disadvantage with the former method of performing a batch protocol is that the entire reagent microplate is processed during the batch run, which may lead to unused and wasted reagents if number of samples is less than the maximum allowed by the batch. For example, a batch protocol may involve the automation of six different assays (see U.S. patent application Ser. No. 11/363,521 entitled "MICROPLATE ASSAY KIT" filed on Feb. 28, 2006), published as U.S. Patent Publication No. 2007/0202010 which is incorporated herein by reference in its entirety.

The six assays are performed on a column-wise basis, with each assay utilizing two reagents per sample. The reagents are stored in the reagent microplate with one pair of columns per assay so that for any given assay, the first reagent is stored in the odd column and the second reagent is stored in the even column. In each microwell 210 of the reagent microplate, there is a sufficient volume of reagent for dispensing into two microplate wells. The assays are performed in pairs of columns on the reaction microplate, so that up to sixteen samples can be processed per batch. If only one sample is loaded for analysis, then almost all of the reagents are wasted.

This problem can be circumvented by a batch protocol that utilizes an orthogonal approach in which samples are processed serially and assays are performed in parallel on a per-sample basis. For example, a batch protocol of this type may involve eight different assays. Assuming two reagents per assay, the reagents for an assay are stored along a given row of the reagent microplate, with the first reagent in the odd columns and the second reagent in the even columns. The assays are performed in parallel on a column-wise basis, where a single sample is processed in each column. Up to six samples can be measured using a given reagent microplate (alternatively, if a sufficient volume of reagent is present in each microwell of the reagent microplate to dispense into two microwells, then up to twelve samples can be analyzed with a single reagent microplate). If less than the total number of six samples is loaded at the commencement of a sample batch protocol run, then the analyzer can run a batch protocol that measures only the number of loaded samples. This can be done by a variable-size batch protocol that can perform any number of assays up to and including six.

In a preferred embodiment of a variable-size batch protocol, the analyzer microplate punch 111 only punches microwells 210 on the reagent microplate in an on-demand fashion. The reagents are therefore consumed on a per-sample basis and are not wasted if the number of samples loaded is less than the maximum allowed value. In such a case, it may be necessary for the analyzer 100 to track the total time during which the reagent microplate remains within the analyzer as the shelf life of a reagent microplate housed in the analyzer is likely different from the shelf life of the microplate under normal storage conditions (e.g. at 4 degrees C.). It is also important to note that if a partially-used reagent microplate is to be used in a subsequent variable-size sample batch protocol, the analyzer 100 should instruct the operator as to the number of samples that it can process before exhausting the reagent supply, number of available microwells or number of available disposable pipette tips. This is easily achieved by tracking consumption and alerting the operator as to the maximum number of allowable sample per batch when a new variable-sized sample batch protocol is initiated by the operator.

The preceding paragraph described a method of performing a variable-sized sample batch protocol. However, as described above, there must also be a corresponding calibration batch protocol in order to produce and retain a dose-response curve for each assay in the batch protocol. The calibration batch protocol corresponding to the variable-size sample batch protocol is also performed much in the same manner as in the sample batch protocol, with the exception that standards from a calibration microplate are pipetted in the place of samples.

In a preferred embodiment, assays are performed serially when performing a calibration batch protocol. One set of assays for a common analyte are performed in parallel, whereby a set of standards having concentrations of a common analyte are measured. This step is then repeated serially for all assays, facilitating the determination of dose-response curves for each assay. In this particular embodiment, the one or more reagent microplates used by the calibration batch protocol may differ in format from the one or more reagent microplates.

In another embodiment, the batch calibration protocol assays are performed in parallel as in the variable-size batch protocol, whereby parallel assays are repeated a number of times with multiple standards with a known analyte concentration. The parallel assays are repeated until a sufficient number of standards have been measured to construct dose-response curves for the assays. In this embodiment, it may be feasible to use a common reagent microplate for both the variable-size sample batch protocol and the corresponding calibration batch protocol.

The calibration batch protocol specifies that this process is repeated with different analyte concentrations each time for each assay. The number of times that the parallel assays are repeated depends on the availability of reagents and microwells within the reagent and reaction microplates. For example, in the example considered in the previous paragraph, the parallel assays could be repeated six times, providing six different data points (assay signals and known concentrations) per assay for all eight assays. The resulting assay signals obtained from the different standards for each assay are mathematically fitted to obtain dose-response curves for each assay.

Having described a general embodiment of the inventive microplate-based automated analyzer 100 and its preferred methods of operation, a specific embodiment of the analyzer is now described. This embodiment is not intended to limit the scope of the invention, but rather serves to illustrate a preferred embodiment of its implementation.

Figure 5:
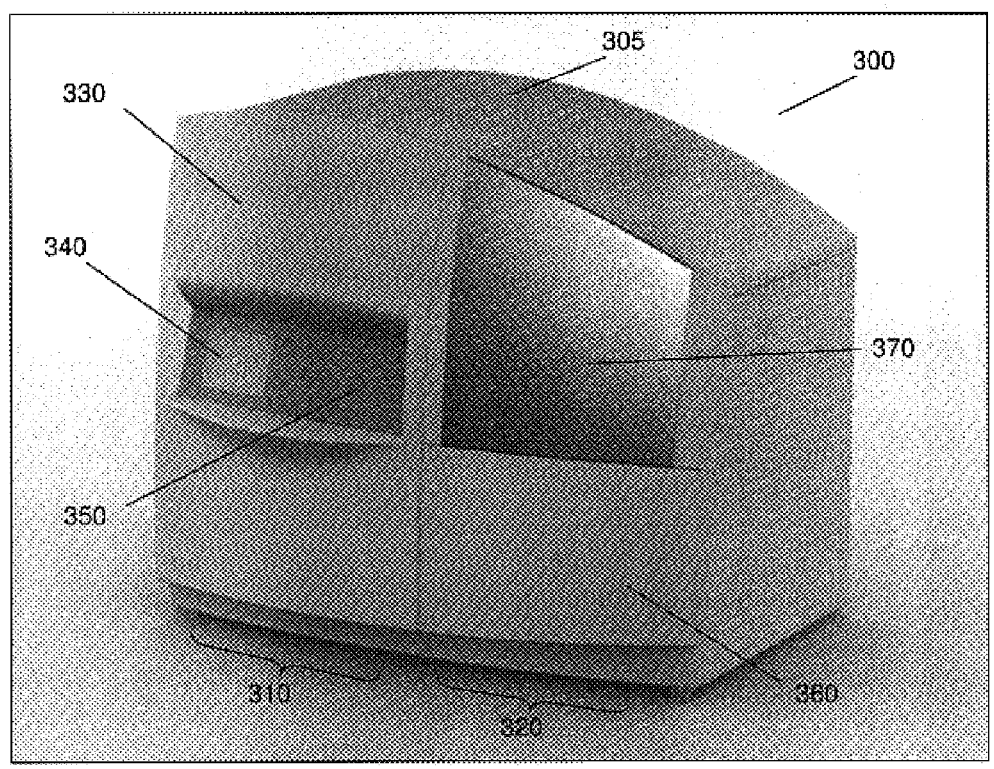
FIG. 5 is a perspective view of a specific embodiment of the analyzer system.

Referring now to FIG. 5, the outer body of an automated analyzer 300 is shown. The analyzer 300 is a compact, single-unit, bench-top device that consumes minimal space in a small clinic or laboratory. The enclosure 305 is made from an opaque material that does not allow the transmission of light within the analyzer 300. The analyzer 300 includes both a main analyzer system 310, where microplates 200 are processed and assays are conducted, and a sample dispensing module 320. In a preferred embodiment, the sample dispensing module 320 is detachable from the main analyzer system 310, allowing the interchange of sample dispensing sections that are configured for different sample types or different sample container formats. The front panel 330 houses both a liquid crystal display (LCD) 340 and a retractable door 350 for loading the analyzer 300 with microplates and other consumables. The LCD 340 is preferably a touchsceen LCD that provides graphical and operator-friendly access to the analyzer's operation and status, as well as a means for the operator to input commands to the analyzer 300. The analyzer further includes retractable sample loading door 360, through which samples are loaded. A semi-transparent window 370 is also optionally provided, enabling the operator to monitor sample processing. If the window is partially transparent, then an optically opaque wall (not shown) is included within the analyzer 300 to separate the main analyzer system 310 from the sample dispensing module 320. An internal door enables the automated transfer of samples from the sample dispensing module 320 to the main analyzer system 310.

Figure 6:
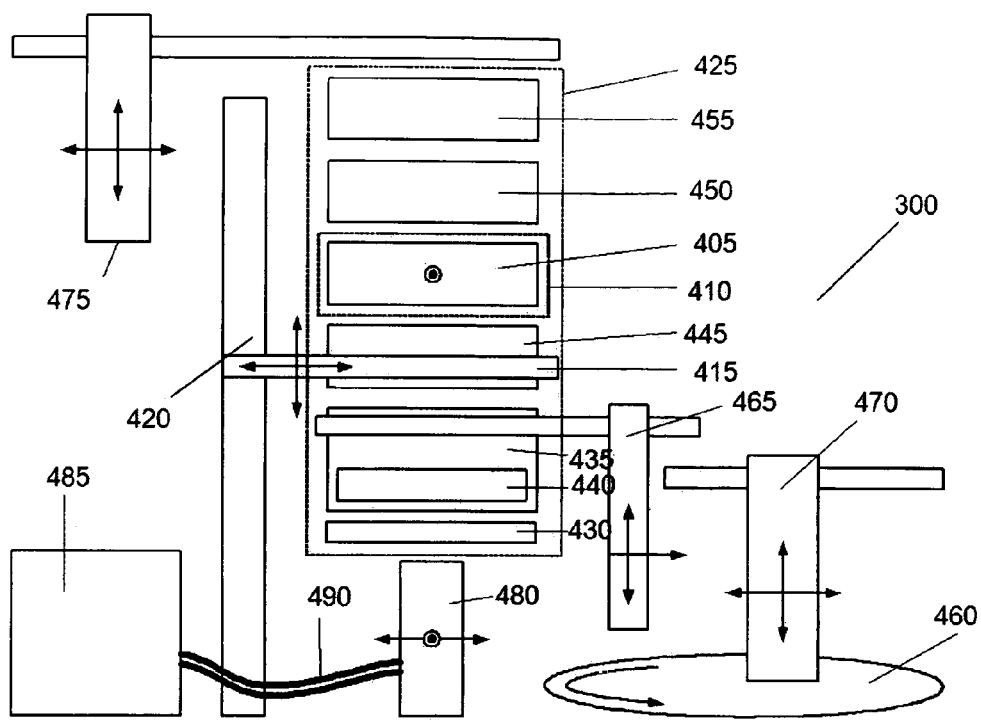
FIG. 6 schematically shows the main subsystems within the specific embodiment of the analyzer.

FIG. 6 illustrates the main components of the analyzer 300 in block diagram form, as seen from the front of the analyzer. The analyzer 300 is loaded with reaction microplates where individual assays are conducted, reagent microplates and disposable pipette tip boxes. A loading arm 405 extends beyond the analyzer opening 410 and accepts microplates and pipette tip boxes from the operator. Situated on the loading arm 405 is a microplate carrier tray that supports and holds microplates and disposable pipette tip boxes. The loading arm 405 can be withdrawn into the analyzer 300 for the internal transport and processing of the microplates and disposable tip boxes. As will be further described below, a carrier tray transport arm 415 engages with microplate carrier trays upon which microplates and pipette tip boxes are placed. A transport assembly 420 capable of horizontal and vertical motion is employed for the transport of carrier trays (engaged by the transport arm) within the analyzer 300 to various processing stations. All subsystems that involve linear motion are driven by stepper motors, preferably fitted with encoder systems for precise tracking of motion. For each motion system in a given spatial dimension, a reference position is established by an opaque finger that passes through a photo-interrupter.

A plurality of carrier tray processing and park positions is located within the analyzer 300. Each carrier tray position provides a positioning means to assist in disengaging a carrier tray from the transport arm. These positions are arranged vertically within the analyzer to allow for random access. An open space, hereby referred to as the transfer zone 425, is provided in front of the vertical arrangement of carrier tray processing and park positions to allow vertical transport of the carrier trays by the transport arm. The lowermost position is the optical detection station 430 where the optical signal produced within or modified by a microwell in a reaction plate can be measured.

Above the optical detection station 430 is the thermal incubator 435, where reaction microplates are thermally incubated during an assay. The incubator incorporates an internal orbital vortexer 440 that provides agitation during incubation. Above the incubator is a secondary vortexer 445 that enables simultaneous and independent agitation of a second microplate (reaction or reagent) outside of the incubator. Above the secondary vortexer lies the plate loader 405, which when fully retracted from the analyzer door 350 (FIG. 6) functions as an additional park position for a carrier tray. Two additional fixed park positions 450 and 455 are also incorporated into the analyzer 300 and lie directly above the loading tray. Optical proximity sensors are included on the plate loader 405 and all park and processing positions for the detection of a carrier tray (in order to verify the present state of a batch protocol and ensure that a carrier transfer was properly conducted). The park positions increase the potential throughput of the analyzer 300 and enhance the random access capability of the analyzer when performing complex assays with inter-plate pipetting.

Unlike traditional analyzers that often require a manual sample preparation step, analyzer 300 includes an automated sample dispensing module that fully automates sample handling. The sample dispensing module is a sample-specific module that interfaces mechanically and electrically with the main body of the analyzer. It is therefore possible to interchange sample dispensing modules to suit the needs of a particular assay, sample type, or sample container type.

The sample dispensing module incorporates a rotating carousel 460 that holds a plurality of sample containers. An automated linear pipette 465 is used to extract a precise volume of sample and transport the sample within the main analyzer system 310, dispensing the sample into a well of the reaction microplate. An optional probe system 470 performs additional measurements on the samples within the sample containers, such as liquid level measurements or electrochemical measurements. Sample containers are identified by a bar-code reader that interrogates the containers as they are rotated. The operator therefore need only open the top of the sample container and place it on the sample carousel 460, thereby eliminating the possibility of transcription errors and additional exposure to the sample by the operator.

Additional liquid handling, including the aspiration and dispensing of reagents and wash buffers, and also the dilution of samples and removal of waste, is performed via an 8-channel automated pipette 475. The multichannel pipette is moved within the analyzer in the vertical and horizontal directions by stepper motors. A long vertical range allows the multichannel pipette 475 to access microplates located within the transfer zone 425 that lie between the optical detection position 430 and the position adjacent to the secondary vortexer 445. With the assistance of the transport arm 415, rapid pipetting between a reagent microplate located on the secondary vortexer and a reaction microplate at the optical detection position 430 is feasible.

The result of an assay is optically interrogated using a scanning optical head 480. In one embodiment, the head 480 is either a single-channel beam than measures luminescence, fluorescence and absorbance. In another embodiment of the invention, the optical head is an 8-channel system that measures the absorbance of a row of eight microplate wells in parallel. The head moves relative to the optical detection position 430 either by scanning the optical head or scanning the optical detection position within a two-dimensional space. The generation of a narrowband excitation or absorbance beam and the filtering and detection of emitted light is performed remotely in second optical subsystem 485 that is interfaced with the optical head 480 via flexible fiber-optic bundles 490.

Figure 7:
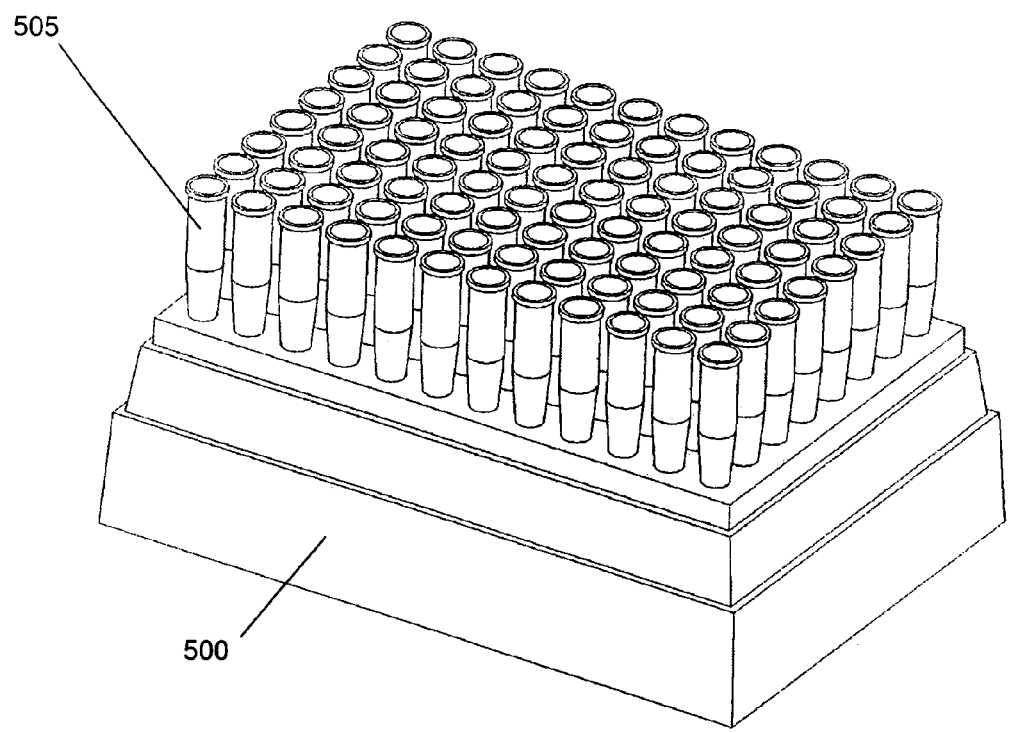
FIG. 7 is a perspective view of a pipette tip box, shown loaded with pipette tips.

As described above, disposable pipette tips are used to simplify the operation of the analyzer and remove the need for tip washing. Shown in FIG. 7 is a microplate tip box 500 containing 96 disposable tips 505. A tip 505 is loaded onto the pipette by moving the pipette downwards onto a given tip (or set of tips in the case of a multichannel pipettor) and applying sufficient pressure. Following the use of a tip, it is disposed into the same location in the tip box by lowering the pipette tip into the selected tip receptacle within the tip box and ejecting the tip from the automated pipette.

Figure 8:
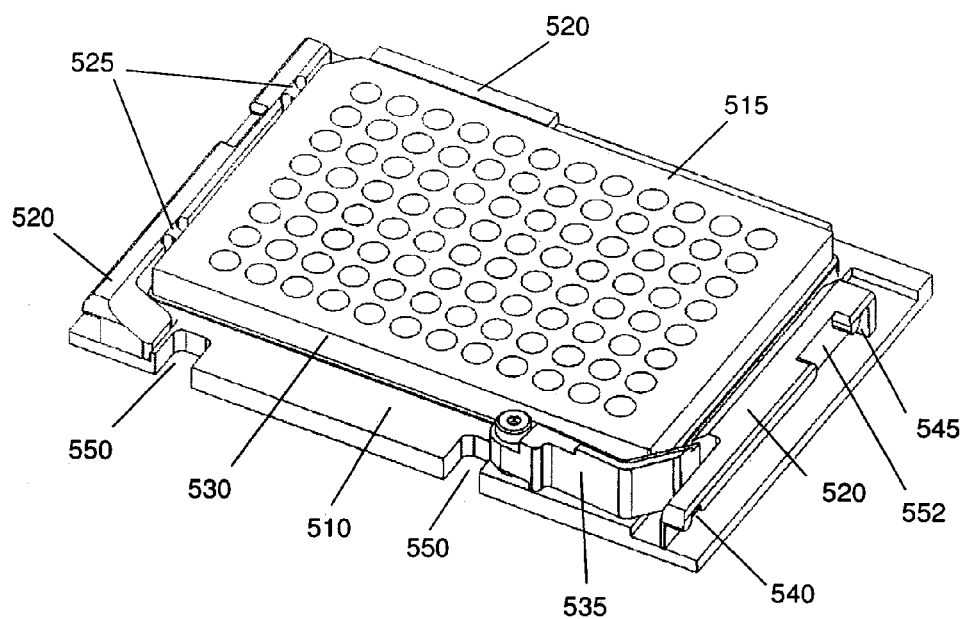
FIG. 8 is a perspective view of a microplate carrier tray with a reagent microplate held in place.

In order to accommodate the accurate transfer of the microplates and the pipette tip box within the analyzer 300, specialized carrier trays are used. FIG. 8 shows a carrier tray 510 designed for use with reagent microplates. In the figure, a reagent microplate 515 is shown housed on the microplate carrier tray 510. The carrier tray 510 includes three positioning bars 520 located on either side and to the back of the microplate 515. Each positioning bar 520 further includes two lateral positioning structures 525 that are employed for the accurate positioning of a microplate 515. The lateral structures butt against the outer microplate flange 530. A plate clamping mechanism 535 is used to firmly and accurately press the microplate flange 530 against the positioning structures 525. The clamping mechanism 535 is a spring-loaded angle-arm that is actuated by the operator to engage or disengage a microplate within the carrier tray 510. Within the outer side of the two positioning bars 520 located to the sides of the microplate 515 are a first 540 and second 545 vertical recess. The two positioning bars 520 to the sides of the microplate 515 each further include a longitudinal gap 552. These vertical recesses 540, 545 and longitudinal gap structures 552 are used to engage a carrier tray 510 with the transport arm. As will be described below, the transport arm incorporates lateral pins that support the carrier tray via the vertical recesses 540 and 545. The carrier tray also incorporates two slots 550 that mate with locating pins on a carrier tray support that receives a carrier tray within the analyzer. A similar carrier tray design is used to support and transfer a microplate disposable pipette tip box within the analyzer.

Figure 9:
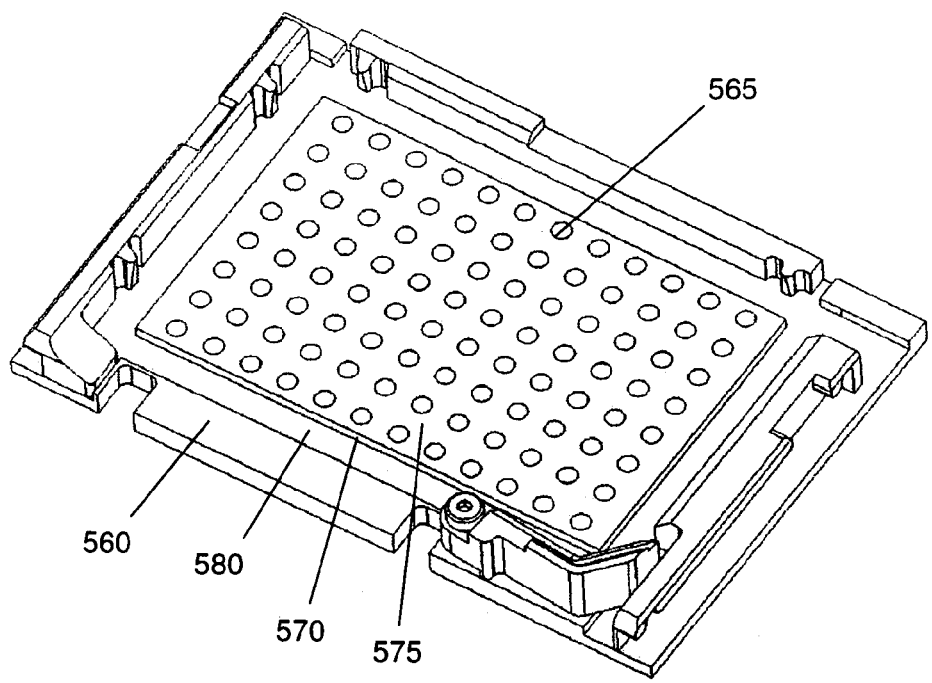
FIG. 9 is a perspective view of a preferred embodiment of a carrier tray for a reaction microplate.

A second type of carrier tray is employed to support the reaction microplate. As previously mentioned, depending on the nature of the optical detection system, it may be necessary for optical radiation to be collected from or directed onto the bottom surface of the reaction microplate 515. This general requirement for access to the bottom of the reaction microplate 515 precludes the use of the carrier tray 510 shown in FIG. 8, where a solid opaque surface lies below the microplate 515. A preferred embodiment of a reaction microplate carrier is shown in FIG. 9 at 560. The carrier tray 560 is very similar in design to that of FIG. 8, with the exception of a plurality of holes 565 extending through the bottom surface of the carrier tray 560. Each hole is located directly below a microplate well, enabling the unobstructed passage of optical radiation. In a preferred embodiment, the carrier tray 560 is made of a thermally conductive material such as aluminum or copper.

In addition, the thickness of the carrier tray 560 is such that a sufficient thermal mass is provided to establish a substantial thermal equilibrium over the two-dimensional area below the microwells of a microplate supported by the carrier tray. Furthermore, the through holes 565 are located in a raised section 570 of the carrier tray surface, in such a manner as to ensure the close proximity of the upper surface 575 of the raised section 570 to the bottom surface of a microplate well. This is achieved by the ensuring that the microplate flange 220 contacts only the outer surface 580 of the carrier tray. The close proximity ensures that the microplate wells are exposed to the thermal equilibrium provided by the carrier tray surface, thereby substantially reducing any thermal gradients that may initially exist among microwells on the supported microplate. In a further refinement of this embodiment, the diameter of the through holes 565 is sufficient to allow the necessary unobstructed passage of optical radiation, but less than the diameter of the bottom surface of the microplate well. This arrangement further improves the thermal interaction between the raised section 575 of the carrier tray and a microplate well.

Figure 10:
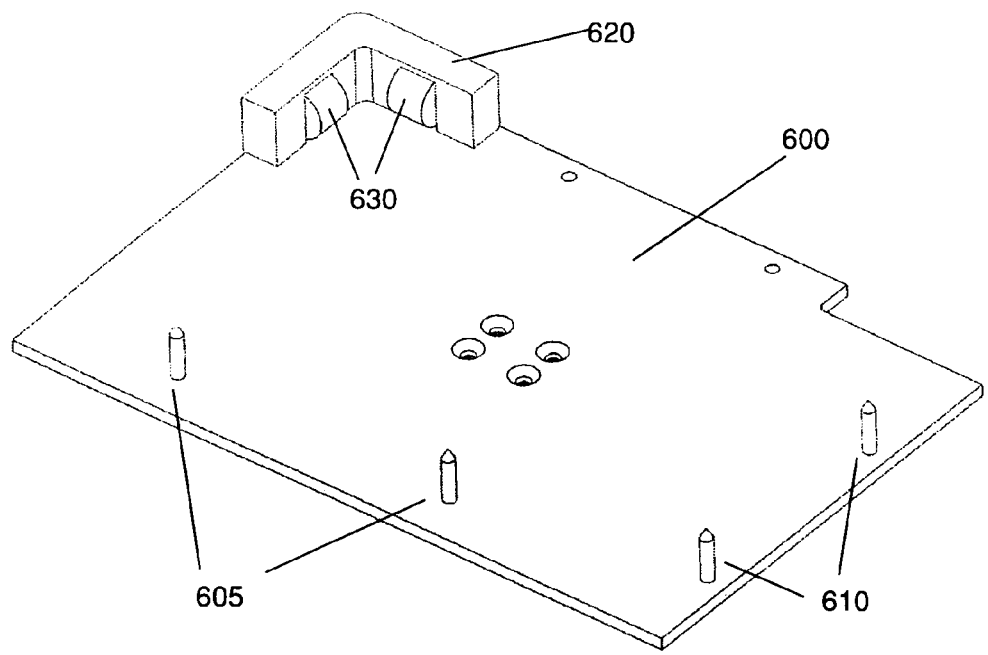
FIG. 10 is a perspective view of a secondary platform that is used to secure a carrier tray in a given location within the analyzer.

FIG. 10 shows a carrier tray support platform 600 that is used to accurately place a carrier tray at a selected park or processing position within the analyzer. The support employs two pairs of locating pins 605 and 610 to precisely fix the position of a microplate carrier tray. The front pins 605 engage with slots 550 on the microplate carrier tray as the carrier tray is lowered onto the support by the transport arm (further described below). The side-mounted pins 610 butt against the vertical edge of the right side of the microplate carrier tray 510. A corner bracket 620 with spring-loaded cylinders 630 is used to firmly hold the carrier tray in place. The cylinders press against the sides of the carrier tray 560, causing the carrier tray 560 to press firmly the carrier tray against the positioning pins 605 and 610 in both horizontal directions, ensuring that the carrier tray 560 is unable to move from its desired position during use. The springs (not shown), located within bracket 620 and behind cylinders 630, also allow easy installation and removal of a carrier tray 560 by the transport arm.

Figure 11:
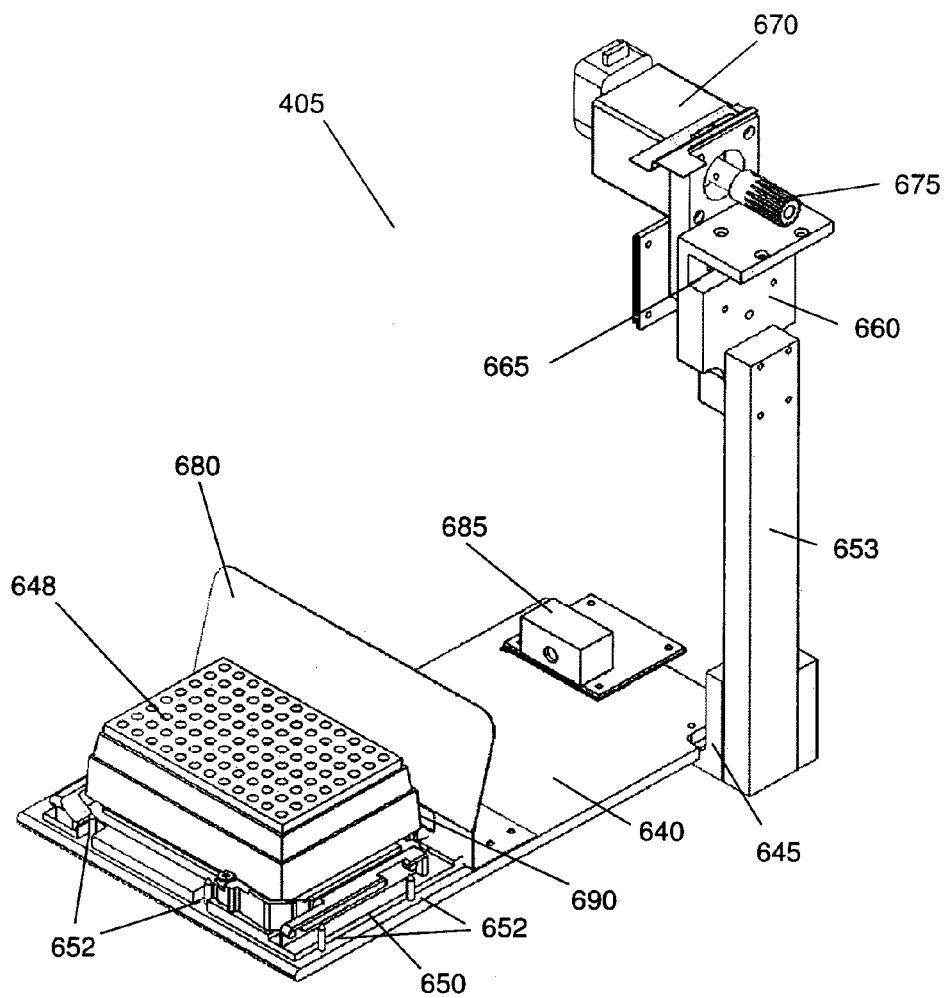
FIG. 11 is a perspective view of the loading arm assembly used to load microplates and pipette tip boxes within the analyzer.

Prior to inserting a microplate 515 or pipette tip box 500 within the analyzer 300, the operator first places the microplate or pipette tip box on a corresponding microplate carrier tray 560 or pipette tip carrier tray. The carrier tray 560 is then placed inside the analyzer 300 via a plate loader that emerges through the analyzer opening 410. The loading arm 405 is shown in greater detail in FIG. 11 and includes a platform 640, a bracket 645 and a vertical bar 653. The loading arm 405 is shown supporting an empty pipette tip box 648. Integrated into the platform 640 is a carrier tray support 650 for receiving a carrier tray 560. As previously described, the carrier tray 560 is accurately held in position by positioning pins 652 and two spring-loaded cylinders in a corner bracket (not shown in the drawing). The bracket 645 and vertical bar 653 position the platform 640 in a suitable position relative to a fixed guide rail (not shown) within the analyzer. A second bracket 660 attached to the vertical rod 653 allows a second horizontal guide rail (not shown) to support the plate loader via a mating slot 665. The mating slot 665 provides a means for the loading arm 405 to slide horizontally along the guide rail, whereby the portion of the platform 640 containing the carrier tray support 650 can be made to protrude through the analyzer door 410 for access by the operator.

A stepper motor 670 operates a rack and pinion drive system for automating the horizontal motion of the loading arm 405. The pinion 675 engages with teeth on a horizontal rack (not shown) for this purpose. As front of the platform 640 of the plate loader assembly is brought in contact with the inside of the analyzer door 410, the door is opened and held in place by an internal spring mechanism. The force of the spring mechanism causes the door 410 to close upon the retraction of the plate loader assembly. The complete closure of the door 410 is detected by an internal Hall sensor. A safety plate 680 blocks access of the operator to the internal area of the analyzer when the loading arm is extended through the door, protecting the operator from internal moving parts and ensuring the integrity of the analyzer.

Upon retraction of the loading arm 405 into the analyzer 300, a barcode reader 685 scans a barcode 222 (FIG. 2) affixed to the rear side of the microplate 220. A horizontal slot 690 in the safety plate 680 provides the necessary visibility of the barcode 222 to the barcode reader 685. The information obtained by scanning the barcode 222 is used to verify that the correct microplate or other consumable was loaded, as per the requirements of a particular batch protocol to be executed by the analyzer 300. In a preferred embodiment, a carrier tray proximity sensor (e.g. an optical or Hall sensor) resides behind the safety plate 680 and detects the presence or absence of a carrier tray 560 through a second slot in the safety plate 680.

Figure 12:
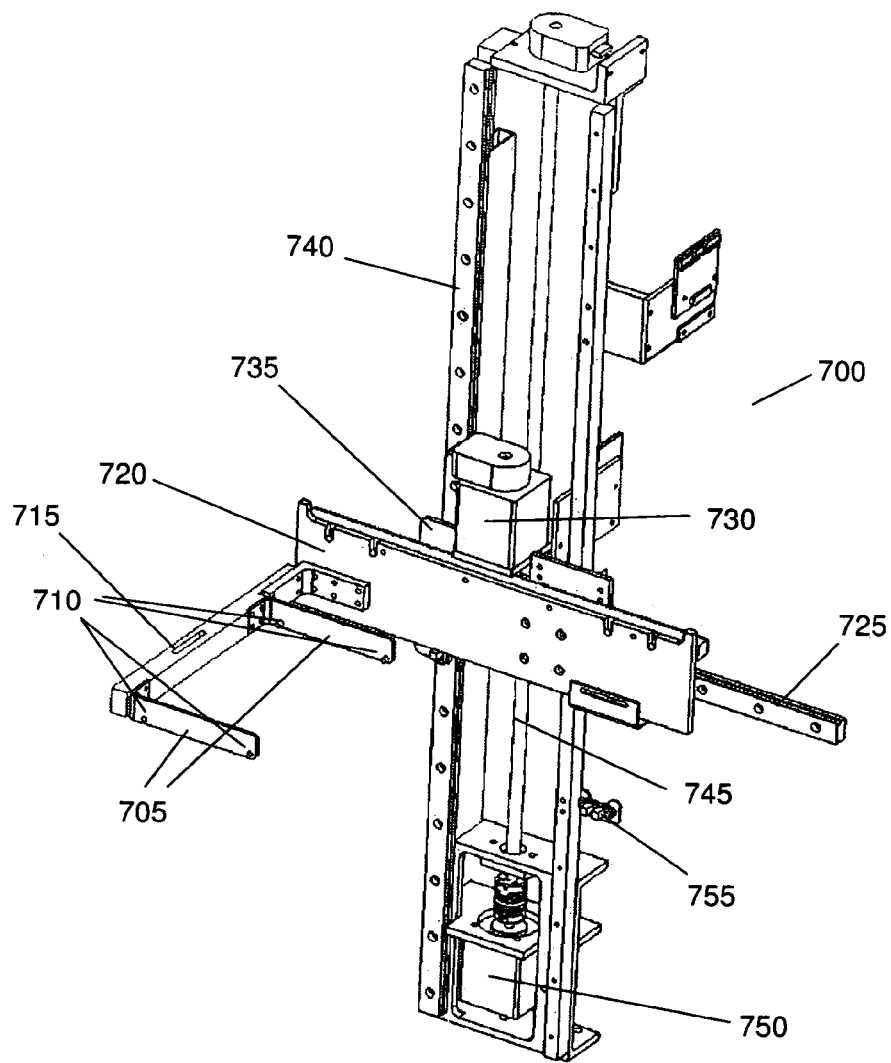
FIG. 12 is a perspective view of the transport arm assembly used to transport carrier trays within the analyzer.

The carrier trays 560 and accompanying microplates or pipette tip boxes are transported to different park and processing positions within the analyzer 300 via a transport arm assembly 700 shown in FIG. 12. The transport arm assembly 700 contains a set of parallel horizontal transport arms 705 that engage with a carrier tray via a pair of support pins 710. A carrier tray 560 housed on a carrier tray support 600 is by engaged by the transport arms 705 by first positioning the transport arms so that the front set of support pins 710 lie in front of the lateral positioning bars 520 (see FIG. 8) and the rear support pins 710 pass through the longitudinal gaps 552 in the lateral positioning bars 520. The transport arms 705 are then moved forward until the support pins 710 are positioned immediately below the vertical recesses 540 and 545 (see FIG. 8) on the lateral positioning bars 520. Finally, the transport arms 705 are raised, bringing the support pins 710 into the vertical recesses 540 and 545 and thereby lifting the carrier tray out of the carrier tray support. By applying sufficient vertical force, the carrier tray 560 presses upon the spring-loaded cylinders 630 in the carrier tray support 600 and is subsequently disengaged. A carrier tray 560 may be placed onto a carrier tray support by reversing the sequence of the aforementioned procedure.

The transport arms 705 are connected by a lateral bar 715, which is attached to a platform 720. The platform 720 is moved in the horizontal direction along a guide rail 725. A rack-and-pinion system (hidden behind the platform 720 in the figure), driven by a stepper motor 730, is employed to automate the horizontal motion of the platform 720.

A finger and photo-interrupt sensor (not shown) are used to establish a reference horizontal position of the platform 720. The horizontal drive system is attached to a second vertical platform 735, which is constrained to move in the vertical direction by guide rail 740. The vertical platform 735 is moved along the axis of an ACME screw 745 by a second stepper motor 750 for high vertical resolution. A second finger (not shown) and photo-interrupt sensor 755 are used to establish a reference position in the vertical direction. The two degrees of freedom provided to the transport arms 710 by the two motors 730 and 750 enables the placement of carrier trays in numerous park and processing stations within the analyzer 300.

Figure 13:
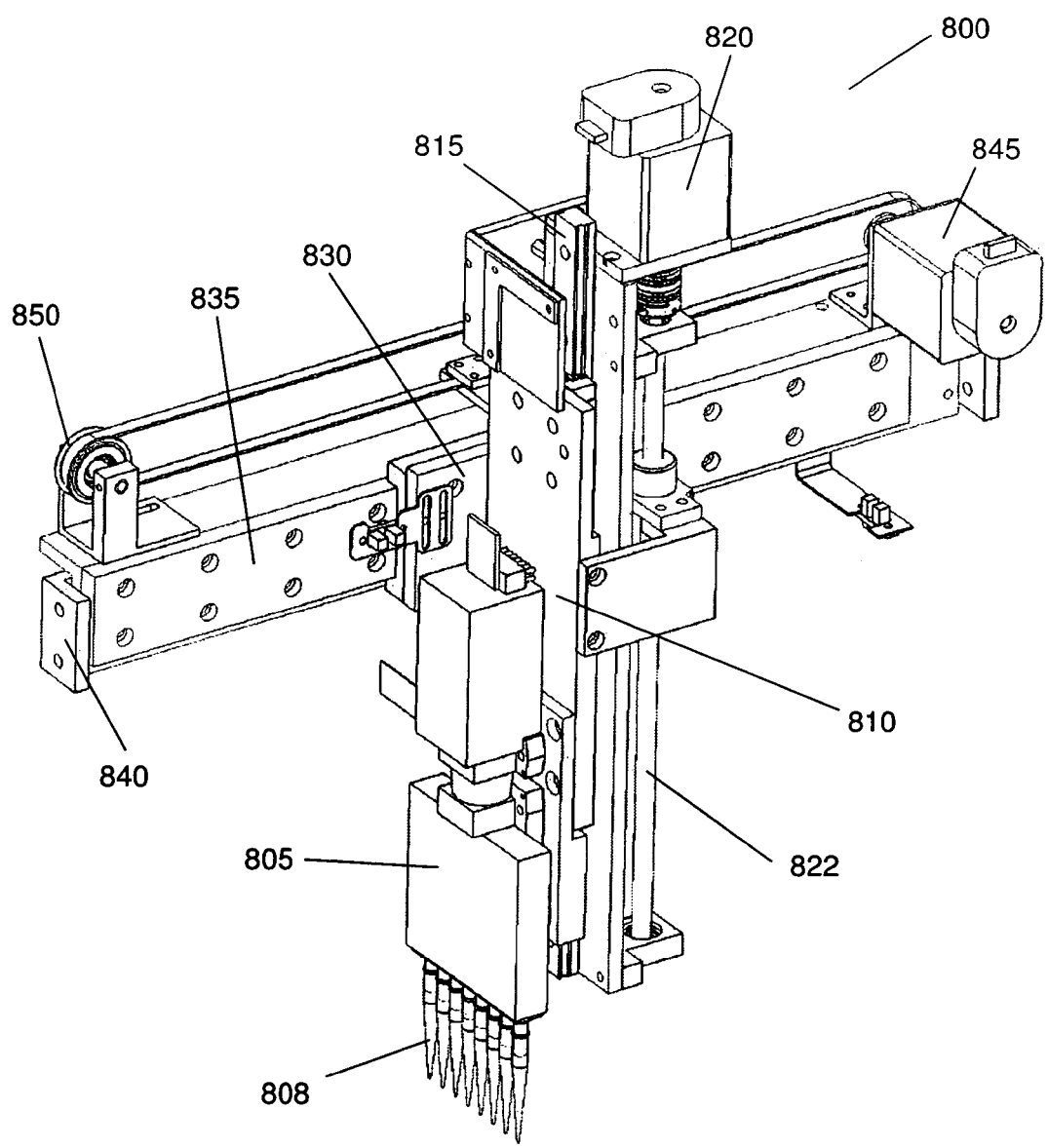
FIG. 13 is a perspective view of the multichannel pipette assembly used for the parallel transport of reagents and buffers.

The aspiration and dispensing of liquids from one microplate 200 to another is performed via an automated multichannel pipette assembly 800, shown in FIG. 13. The automated pipette 805 is an eight-channel air displacement pipette that is commercially available and readily integrated into the analyzer. The multichannel pipette 805 is interfaced to the analyzer processor for automation and is capable of aspiration, dispensing and tip ejection. Pipette tips 808 are attached to the multichannel pipette 805 by lowering the pipette downward onto a row of a pipette tip box and applying sufficient vertical force. Upon raising the multichannel pipette 805, the tips remain attached to the pipette via frictional forces. The tips are ejected by a sheath (not shown) that plunges downwards and pushes on the flange at the proximal end of the tip. The automated pipette is attached to platform 810, which slides vertically along a guide rail 815.

A stepper motor 820 controls the vertical motion of the platform 810 along an ACME screw 825 for precise displacement control. The vertical assembly is attached to a second horizontal platform 830, which slides along a second guide rail 835. The guide rail 835 is mounted on a second fixed horizontal platform 840. The horizontal motion of the pipette 805 is controlled by a second stepper motor 845 that operates a belt and pulley system 850.

Referring to FIGS. 6 and 13, the horizontal degree of freedom enables the multichannel pipette 805 to move in and out of the transfer zone 425, where it can aspirate from or dispense into reagent and reaction microplates and access disposable tips in a pipette tip box positioned in the optical detection position 430. Alternatively, the pipette system can access microplates held by the transport arm assembly 700 (FIG. 12) that are situated above the optical detection position 430 and below the vertical position adjacent to the secondary vortexer 445. The fine pitch of the ACME screw 822 ensures that sufficient vertical resolution is afforded to the pipette 805 for the accurate placement of a pipette tip 808 within a microplate well.

Although the 8-channel automated pipette 805 is designed primarily for 96-well microplates such as microplate 200 in FIG. 2, it can also accommodate liquid handling for a 384-well microplate if additional throughput is desired. This is achieved by adding a translation stage (e.g. a rack-and-pinion drive system) that moves the multichannel pipette 805 in a direction that is parallel to the row of individual pipettes. In this manner, the 8-channel pipette 805 first addresses rows 1, 4, 8, 12, 16, 20, 24, 28 and 32, and then rows 2, 5, 9, 13, 17, 21, 25, 29, 33, and so on. The additional motorized translation stage must provide sufficient precision and accuracy to place the pipettes within the centers of the small wells 210.

Figure 15:
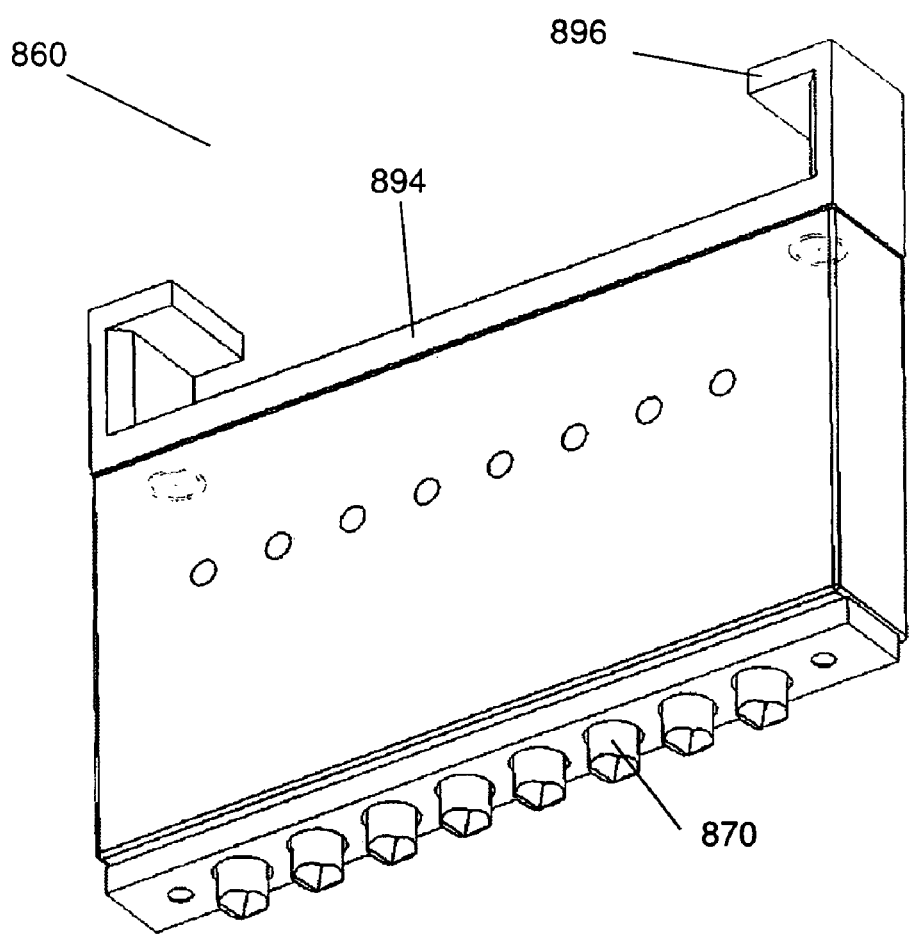
FIG. 15 is a perspective view of a microplate punch tool used to pierce the seals in a column of eight microwells residing in a sealed microplate, where the compression bar is shown in its retracted position.

After loading a sealed microplate 200 into the analyzer 300, the seal must be broken before the multichannel pipette 805 can be used to aspirate internally stored reagents or standards. Many methods of piercing microplate seals are known in the prior art, including the use of single and multichannel piercing tools and the use of pipette tips. The piercing of a microplate seal in the present analyzer is preferably accomplished using a row of puncture pins suitably designed to minimize the punching force and create a sufficient opening for subsequent insertion of a pipette tip. FIG. 15 shows a preferred embodiment of such a punch tool. The punch tool 860 comprises a main housing 865 into which a series of puncture pins 870 are fixed. The puncture pins 870 may be separated or joined together to form an integrated array. Each puncture pin 870 is housed in an individual hollow shaft, although the pins may be mutually connected as described above. The puncture pins 870 preferably have a distal end that is chiseled with three or more facets, where adjacent facets meet along sharp lines that meet at a common vertex. This encourages the formation of cut lines in a sealed surface upon piercing action, and reduces the risk of a misaligned pipette tip experiencing a large compressive force from an unpierced section of the seal surface during subsequent aspiration from a locally pierced microwell.

Figure 14:
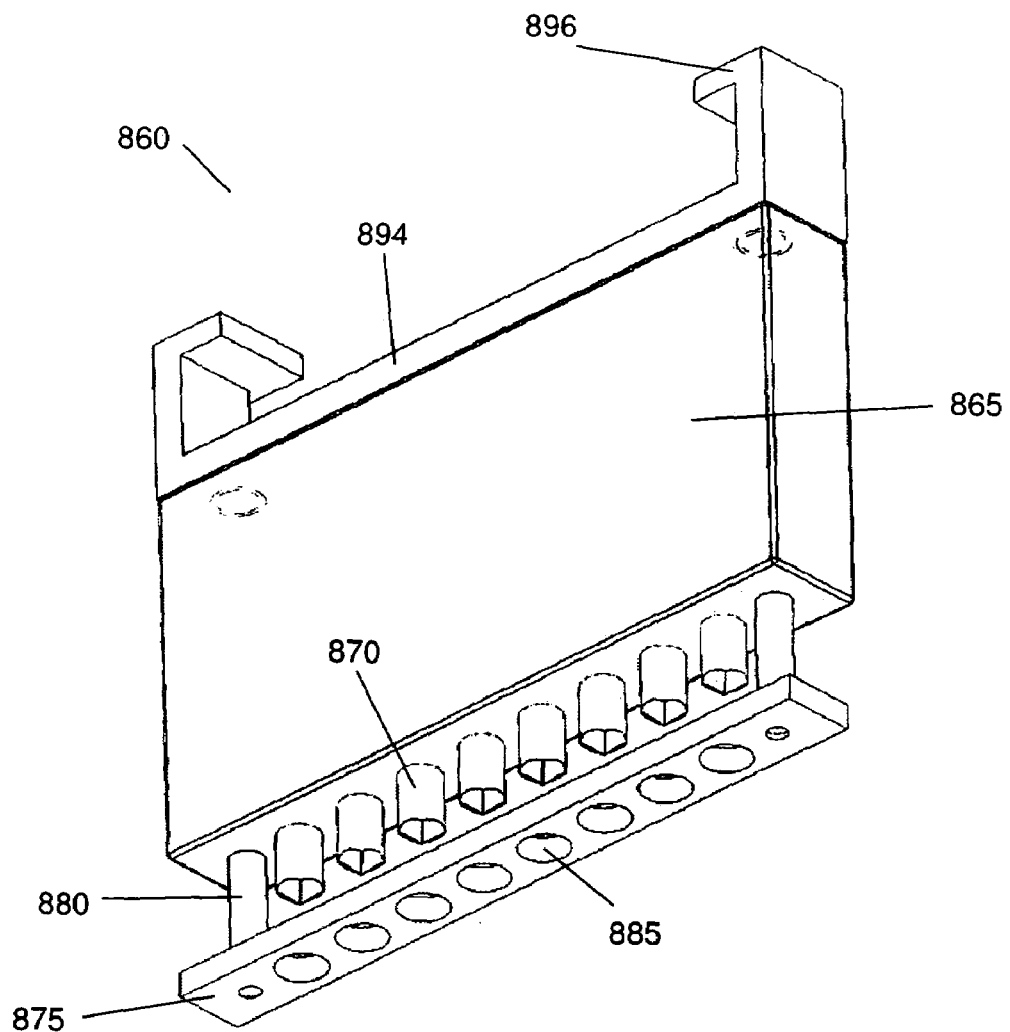
FIG. 14 is a perspective view of a microplate punch tool used to pierce the seals in a column of eight microwells residing in a sealed microplate, where the compression bar is shown in its extended position.

The piercing tool 860 further includes a compression bar 875 that is connected to the main housing 865 via two spring-loaded rods 880. The compression bar 875 is normally forced outward by the force of the internal springs, as shown in FIG. 14. However, when the tool is directed downwards onto the sealed surface of a microplate (so that the puncture pins 870 are aligned with the axes of the microwells within a chosen column), the compression bar 875 impinges upon the upper surface of the microplate and makes contact with the upper flanges of the individual microwells. As the piercing pins 870 descend through the seal and into the microwells, the compression bar 875 is forced upwards towards the main housing 865 and the puncture pins 870 move through the plurality of holes 885 in the compression bar 875. If the puncture pins 870 are maximally extended into the microwells, the compression bar 875 comes into contact with the lower surface of the main housing 865. Such a situation is shown in FIG. 15, where the compression bar 875 is fully compressed against the main housing 865 (the microplate is not shown in order to provide a view the puncture pins). As the puncture pins 870 are withdrawn from the microwells, the compression bar 875 advantageously maintains a downward force on the microplate until the puncture pins 870 have been fully withdrawn. This compressive force ensures that the microplate is not lifted out of its carrier tray during the removal of the puncture pins 870.

Figure 16:
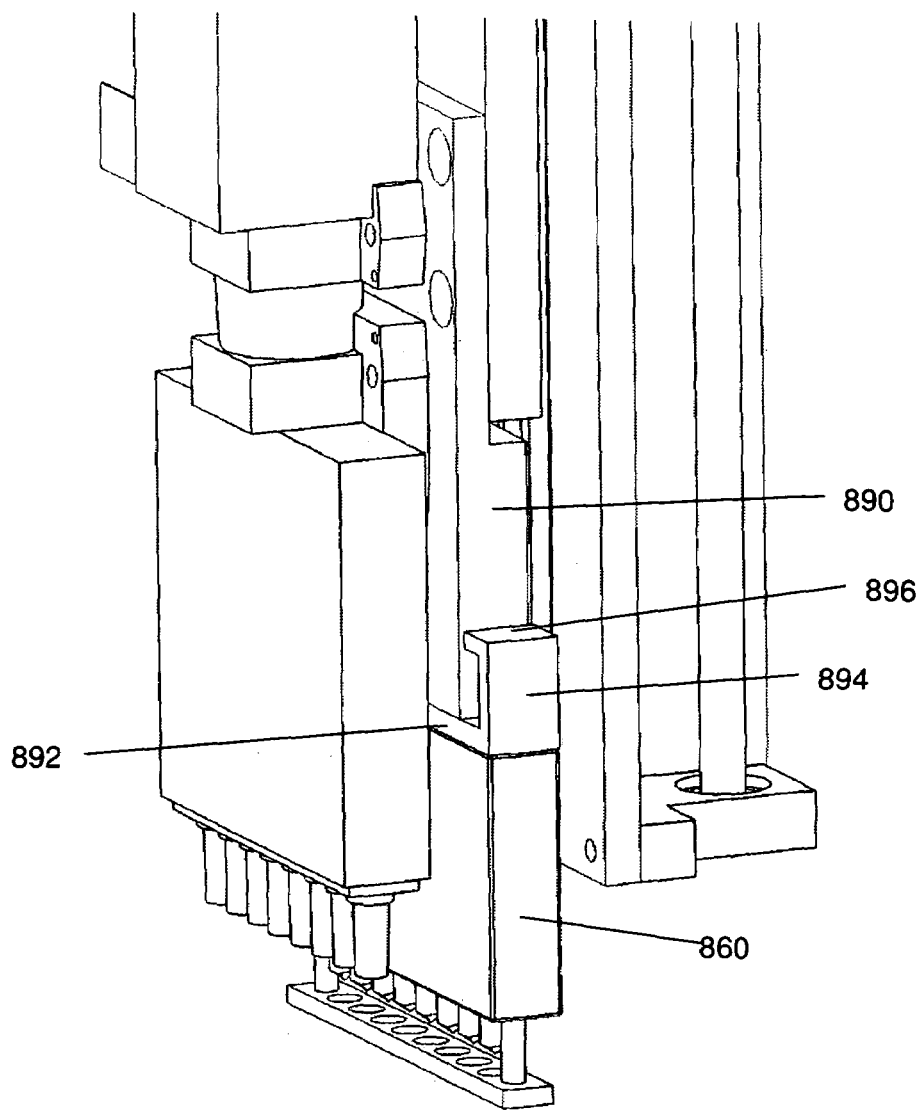
FIG. 16 shows a perspective view of a preferred embodiment of how the punch tool is transported within the analyzer.

In a preferred embodiment, the punch tool 860 resides within the analyzer and is transported via the multichannel pipettor 805 in a piggyback fashion. Such an arrangement is illustrated in FIG. 16, where the punch tool 860 is shown connected to the multichannel pipettor 805. The punch tool 860 may be permanently mounted to the pipettor 805 (provided that sufficient spatial clearance is provided for picking up pipette tips) or alternatively the punch tool may be removable from the pipettor. In an exemplary embodiment, the punch tool 860 temporarily adheres to the pipettor 805 via a mating bar 890 that resides between the multichannel pipettor 805 and the platform 810. The mating bar 890 contains at least one permanent magnet recessed inside its bottom edge 892. The permanent magnet attracts a similar permanent magnet (with opposite polarity) recessed within the upper surface of the support bracket 894 of the punch tool, whereby the force of attachment is sufficient to maintain the connection during all required punching operations. The punch tool may be dropped onto a holder within the analyzer by contacting the extensions 896 of the support bracket 894 with protrusions on the holder (not shown) and applying sufficient force to disengage the magnets.

Figure 17:
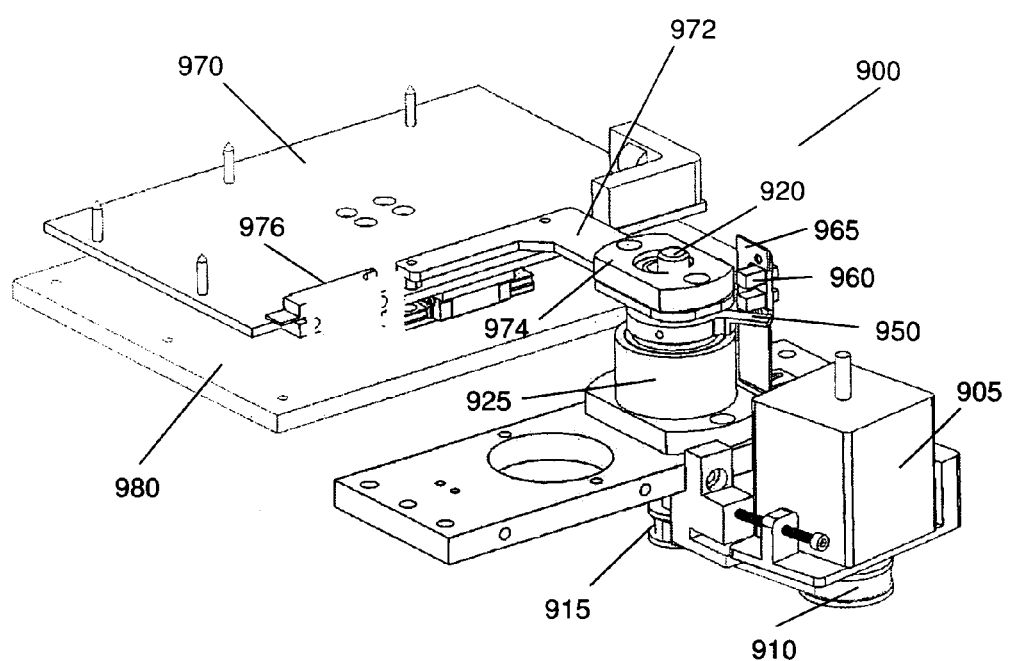
FIG. 17 is perspective view of the vortexer.

FIG. 17 shows the vortexer subsystem 900 employed in the analyzer 300. The vortexer 900 employs a stepper motor 905 to impart an orbital motion to a microplate. The stepper motor 905 directly rotates a drive pulley 910, which in turn drives a slave pulley 915 via a belt drive. The slave pulley 915 is coupled to a shaft 920 that rotates about its primary axis. The shaft 920, which extends upwards from the slave pulley 915, is held by a bearing housed within a flange 925.

Figure 18:
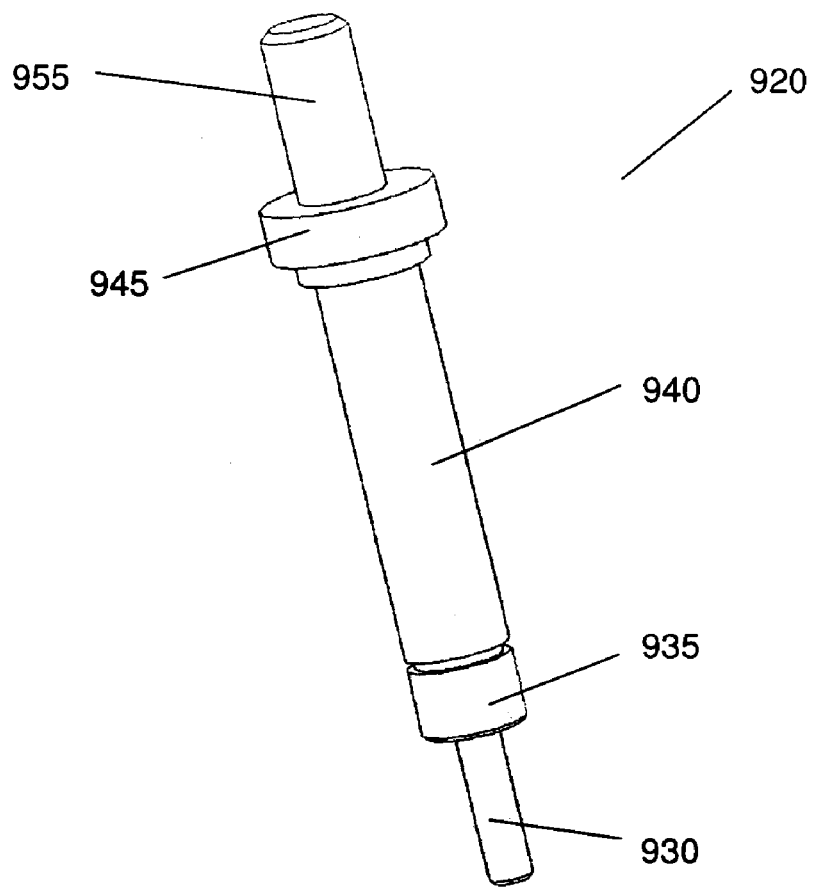
FIG. 18 is a perspective view of the shaft used to produce orbital motion within the vortexer.

The shaft 920 is shown separately in FIG. 18 and includes a plurality of axial sections. The slave pulley 915 attaches to the distal end of the axial shaft section 930. A nut threads onto the neighbouring axial section 935 to provide a means for vertically stabilizing the shaft within the flange 925. Bearings within the flange contact the elongated section of the shaft 940. A wide collar 945 also enables vertical confinement of the shaft within the flange and provides a surface for the attachment of a position-sensing finger 950 (see below). The axial sections 930-945 share a common axis (the primary axis) about which the shaft rotates when actuated by the stepper motor 905. The final axial section 955 has its axis radially offset from the primary axis in order to provide an orbital motion. In the embodiment shown in FIG. 18, the off-center section 955 of the shaft 920 has a diameter of 10 mm and a radial offset (and hence orbital radius) of 0.5 mm. In a preferred embodiment, the orbital radius lies within 0.5 and 7.5 mm.

Referring again to FIG. 17, a position-sensing finger 950 attached to the axis of the shaft 920 is employed to establish a reference angular position and monitor the orbital frequency of the vortexer. The finger passes through a photo-interrupt sensor 960 that is mounted on a separate bracket 965. An additional carrier tray proximity sensor 976 detects the presence or absence of a carrier tray on the carrier tray support 970.

The motion of the upper off-center section 955 of the shaft 920 is transferred to a carrier tray support 970 via a horizontal linkage 972. An additional fixture 974 that contains a bearing couples the linkage 972 to the off-center shaft 920. The bearing smoothly transfers the motion of the off-center shaft to the linkage while completely decoupling the rotary motion of the shaft.

Figure 19:
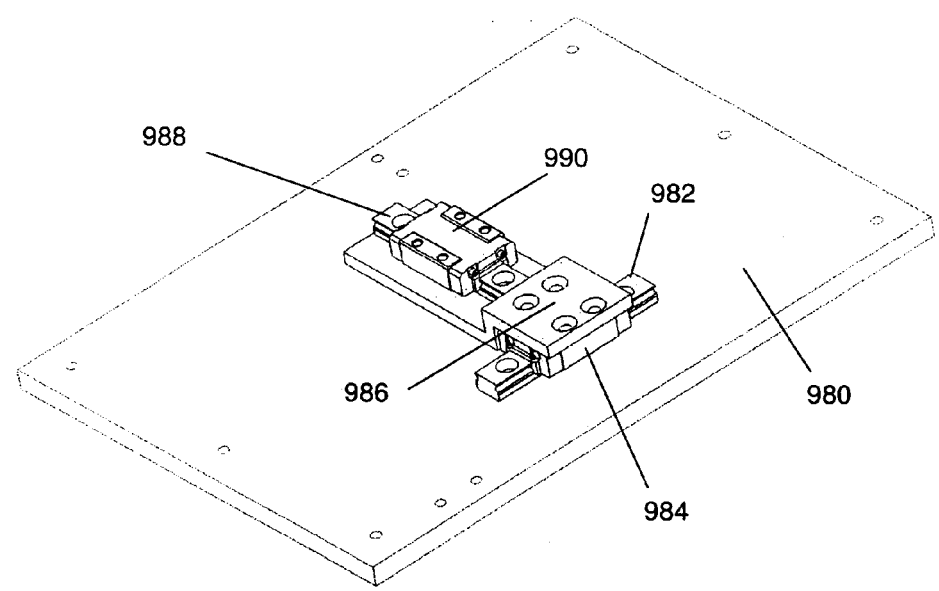
FIG. 19 is a perspective view of two orthogonal linear translation stages employed within the vortexer system for the purpose of confining the motion of the carrier tray support to an orbital profile.

The motion imparted from the shaft to the carrier tray support 970 is constrained to an orbital form via a pair of translation stages located below the carrier tray and attached to the vortexer platform 980. This can be further understood with reference to FIG. 19, which shows only the platform 980 and the translation stages, with the rest of the vortexer components artificially removed. The orthogonal translation stages comprise a first rail 982 fixed to the upper surface of the platform 980. A movable carriage 984 slides freely along the longitudinal axis of the rail 982. A bracket arm 986 is attached to the upper surface of the movable carriage 984 and also supports a second orthogonal rail 988. The bracket arm 986 does not directly contact the upper surface of the platform 980. A second movable carriage 990 moves freely along the longitudinal axis of the second rail 988. Finally, the lower surface of the carrier tray support 970 (shown in FIG. 17 only) is connected with the upper surface of the second movable carriage 990. In this configuration, the orbital motion of the axis of the off-axis section 955 of the shaft 920 is directly imparted to the carrier tray support 970 via the constraints imposed by the translation stages. Furthermore, the orbital radius of the carrier tray support 970 is equal to the radial offset of the two shaft axes 940 and 955.

Figure 20:
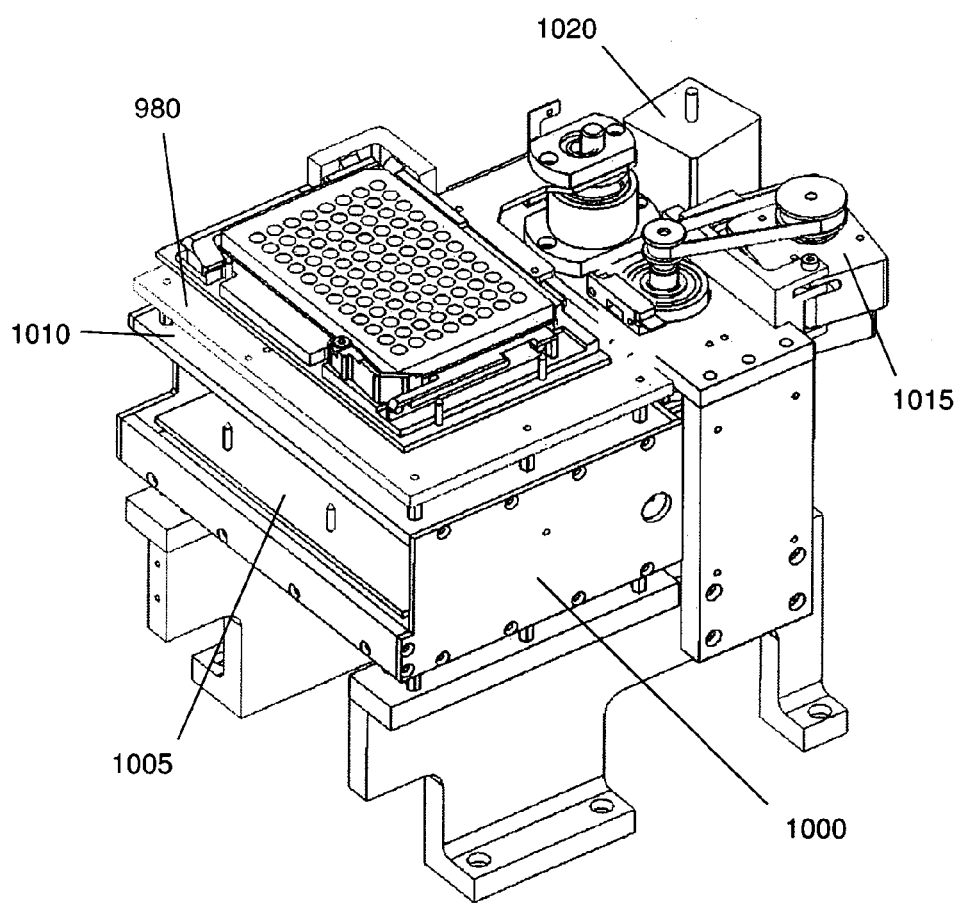
FIG. 20 is a perspective view of the complete vortexer and incubator assembly, showing both the internal and external vortexers.

Also included in the analyzer 300 is a thermal incubator that provides a closed environment with precise temperature control. FIG. 20 shows the incubator 1000 housing a carrier tray support 1005. The incubator 1000 lies immediately below the vortexer system 900, whereby the vortexer platform 980 is located above the upper surface 1010 of the incubator 1000. The incubator may be outfitted with insulating foam sheets (not shown) for enhanced thermal isolation. Attached to the top surface 1010 of the incubator enclosure is a heating element. The upper heating element is preferably a thin kapton surface heater, but may also be replaced with other heater technologies known in the art.

For example, a Peltier thermoelectric cooler can be included in place of or in addition to the heaters to enable cooling of the oven. Alternatively, forced air can be employed for rapid cooling and accurate temperature control. Within the incubator 1000, a second vortexer, the internal vortexer, supports a carrier tray 1005. The internal vortexer enables orbital agitation of a reaction microplate during incubation, which is required for some assay types. The vortexer linkage emerges through the back wall of the incubator and is attached to a shaft as in FIG. 17. As previously described, the shaft is rotated by a stepper motor that drives a dual pulley system. In the embodiment shown in FIG. 20, the axle assembly 1015 (including the motor, pulley system, flange and brackets) is inverted relative to main vortexer axle assembly 1020.

A retractable door (not shown) opens the incubator 1000 for the insertion of a microplate-loaded carrier tray by the transport arms 710. The internal carrier tray support 1005 that forms the top surface of the internal vortexer also includes a rectangular metal platform (not shown) that acts as a large and uniform thermal mass directly below the microplate wells. In a preferred embodiment, the top surface of the metal platform lies within 1 mm of the bottom surface of a reaction microplate well. A second heater is placed below the secondary platform in order to provide a more uniform temperature distribution.

In a preferred embodiment, the heater is directly attached to the bottom surface of the carrier tray support 1005, enabling a direct path of low thermal resistance to the metal platform. In a less preferred embodiment, the heater is applied to the bottom surface of the horizontal platform of the internal vortexer. The internal temperature of the incubator is regulated via feedback from a collection of temperature sensors placed within the incubator 1000. In a preferred embodiment, there are at least two temperature sensors on the incubator side walls and two temperature sensors both above and below the microplate.

Figure 21:
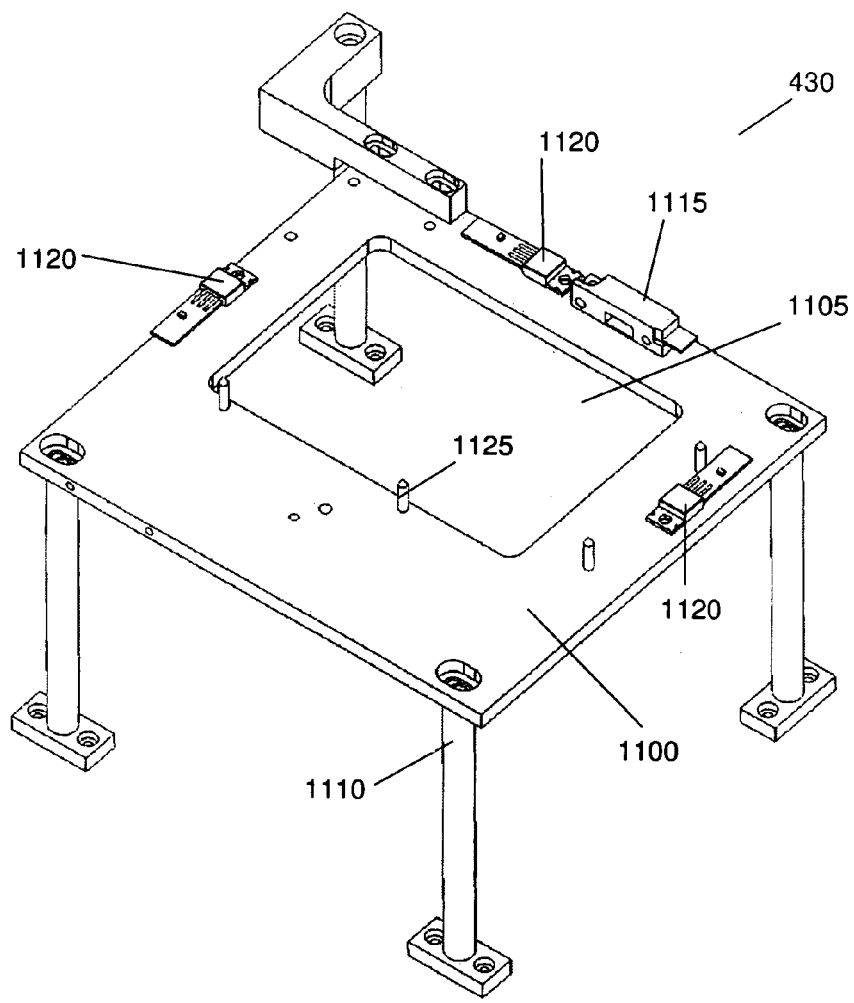
FIG. 21 is a perspective view of the optical detection station.

FIG. 21 shows an embodiment of the optical detection station 430. The station comprises a platform 1100, through which a broad opening 1105 exists to enable the passage of optical radiation to or from the bottom of a microplate to a scanning optical head located below the platform 1100. The platform is supported by four spacer rods 1110, which provide a sufficient gap below the platform to allow for the passage of a scanning optical head. The platform 1100 further includes a carrier tray sensor 1115 for detecting the presence or absence of a carrier tray, and a collection of temperature sensors 1120 for the purpose of measuring the local temperatures and thermal gradients. A set of guiding pins 1125 enables the precise positioning of a carrier plate on the platform 1100. In this embodiment, the carrier plate is preferably further held in place via the transport arms 710.

Figure 22:
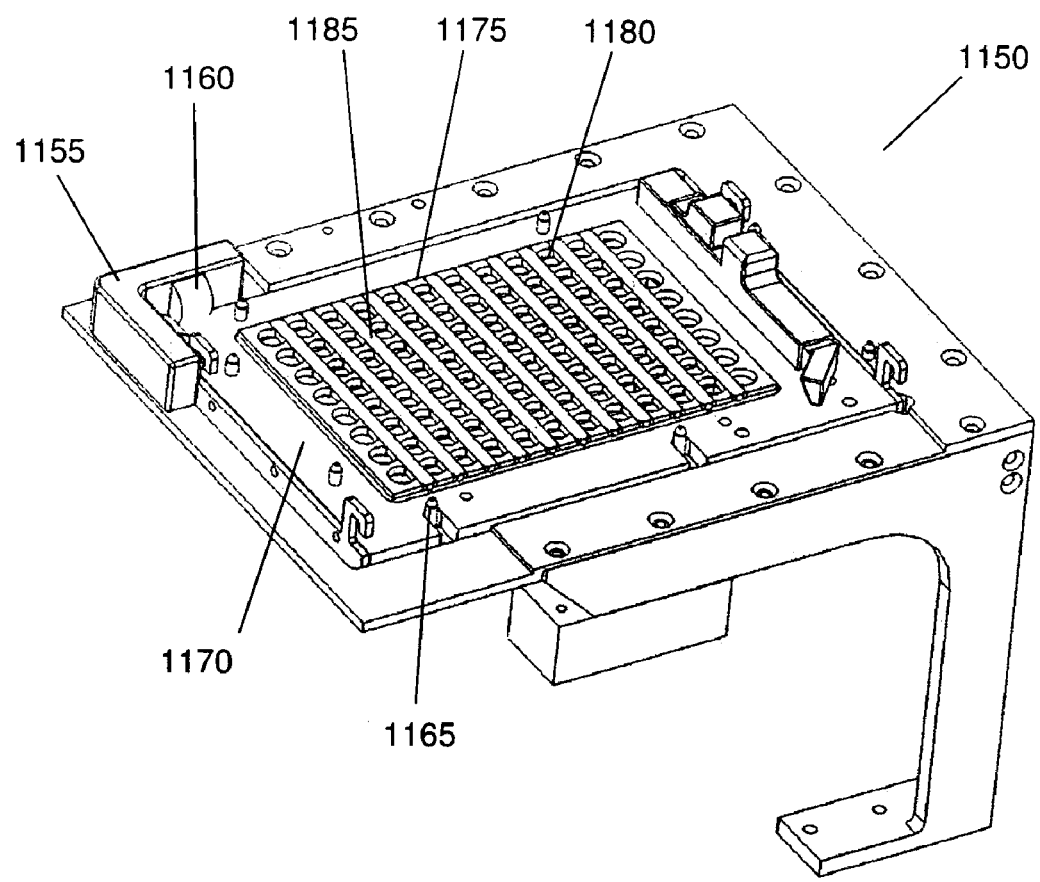
FIG. 22 is a perspective view of another embodiment of the optical detection position assembly shown with a magnetic secondary platform.

In order to enable the use of a parametric solid phase for sample extraction, DNA extraction, DNA assays or heterogeneous immunoassays, one embodiment of the invention incorporates a magnetic separation array into the carrier tray support of the optical detection station. FIG. 22 shows the modified optical detection station 1150, which includes a magnetic carrier tray support. The carrier tray support is in this embodiment shown with a corner positioning bracket 1155 with spring-loaded cylinders 1160 and four positioning pins 1165 for the accurate placement of a carrier tray. In the figure, a microplate carrier tray 1170 (without a microplate) is shown engaged with the carrier tray support. The microplate carrier tray in this embodiment does not contain a plurality of through holes for each microplate well, but instead a single large rectangular aperture.

Unlike the carrier tray shown in FIG. 10, the magnetic carrier tray of FIG. 22 includes a raised rectangular area 1175 that emerges through the aperture in the microplate carrier tray. An array of 96 holes 1180 with a diameter sufficient to allow the passage of optical radiation is provided within the raised rectangular area 1175.

An array of thin magnetic rods 1185 is placed within trenches that lie between rows of holes 1180. In a preferred embodiment, the magnetic rods and have a width of less than 3 mm and a depth of less than 2 mm to prevent the shadowing of emission light from a liquid sample within a microplate well. The thickness of the rectangular area supporting the array of magnetic rods is preferably less than 3 mm for this same reason. The top surfaces of the magnetic rods 1185 all lie in the plane of the top surface of the raised rectangular area 1175.

In a preferred embodiment, these top surfaces are coplanar with the bottom surfaces of the microplate wells when a microplate is placed on the carrier tray. In this manner, the magnets 1185 are disposed as close as possible to a magnetic solid phase that is present within a microplate well. The magnetic field within the well then acts on the magnetic solid phase, drawing it to the side of a well that is closest to the neighboring magnetic rod. The local concentration of the solid phase at a specific region within the well then provides an effective means for separating the solid phase from the liquid by aspirating the liquid with a pipette. The solid phase may then be washed by dispensing a wash buffer into the well and, if required, re-suspending the solid phase within the liquid using the vortexer. If the absorbance, fluorescence or luminescence of the liquid is needed for the measurement of an assay result, the magnetic platform can be used to draw the interfering solid phase away from the bulk liquid for an accurate optical measurement.

In order to overcome the disadvantages of sample handling methods in the prior art, the specific embodiment of the invention incorporates a fully automated sample dispensing module. This module enables the automated transfer of a precise sample volume from an original sample container into a well of a microplate within the main analyzer system 300. This separate module interfaces mechanically and electrically with the main body of the analyzer and is specific to a type of sample container. A separate sample dispensing module may be used for different sample types or sample containers as necessary. For example, individual modules may exist for samples comprising blood, urine or saliva. If the operator wishes to perform analysis on a new sample type, the current sample dispensing module is replaced with the sample dispensing module that supports the new sample type. The mechanical interfacing preserves a light-tight analyzer interior for optimal optical performance.

A preferred embodiment of the sample dispensing module is henceforth disclosed via a non-limiting example involving the analysis of urine samples. In this particular example, the sample dispensing module supports both microplate assays performed within the main analyzer system 300 and also provides an ion selective electrode probe station within the sample dispensing module.

Figure 23:
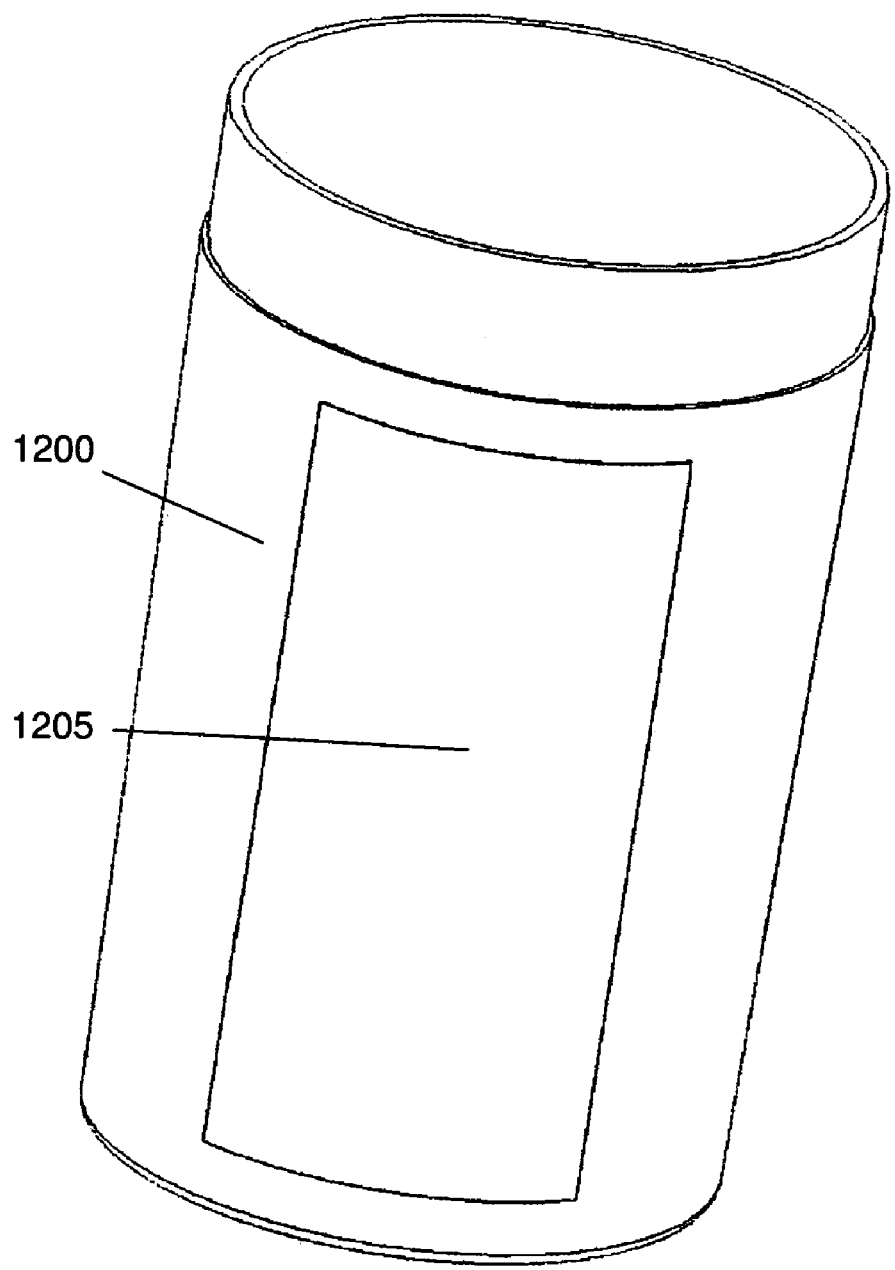
FIG. 23 is a perspective view of a sample collection bottle with bar code label.
Figure 24:
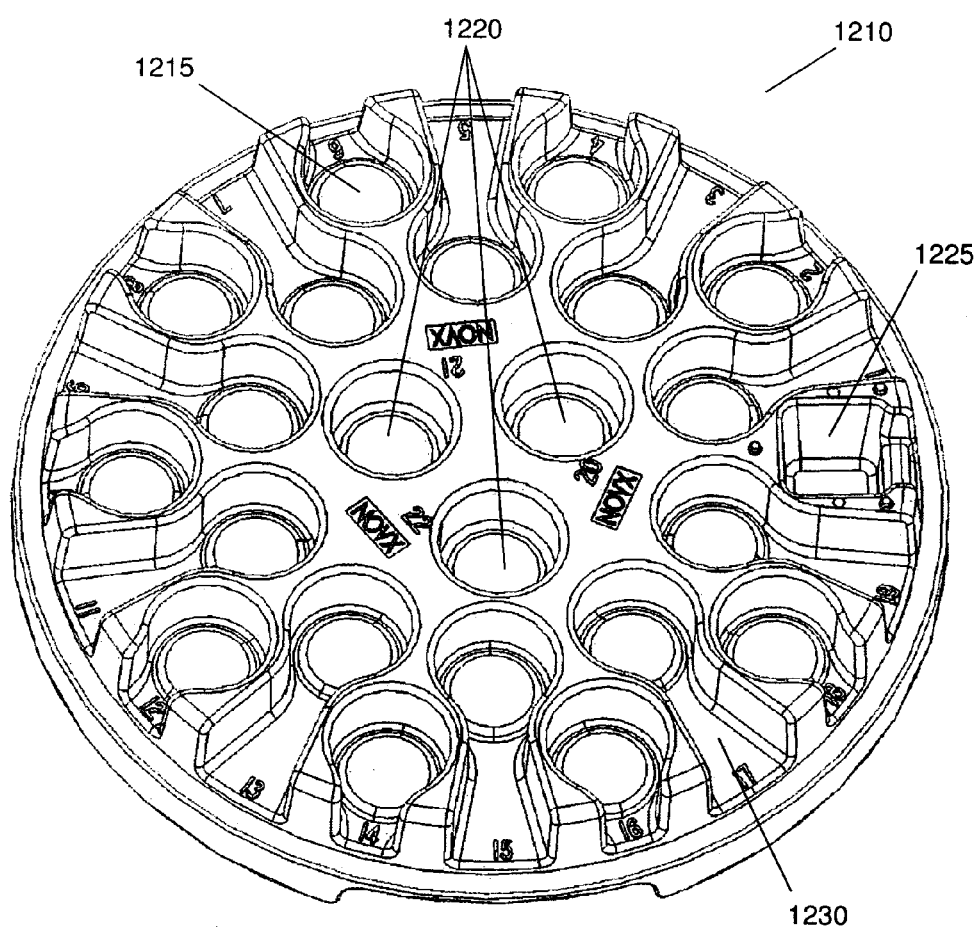
FIG. 24 is a perspective view of the carousel used to hold and position sample bottles within the sample dispensing module.

A urine sample is collected in a standard sample bottle 1200, shown in FIG. 23. Affixed to the side of the bottle 1200 is a bar code label 1205 that uniquely and confidentially identifies the sample and also provides a list of assays to be performed on the sample. Sample bottles 1200 are placed in a sample carousel 1210, shown schematically in FIG. 24. The carousel 1210 contains two azimuthal rows of cylindrical recesses 1215 that accept up to 19 barcoded standard sample bottles 1200. In addition to the 19 sample bottle recesses 1215 are three central recesses 1220 that also accept standard bottles 1200. A tray of disposable pipette tips may be inserted into a rectangular recess 1225 within the carousel 1210 to provide a clean tip to the dispensing pipette each time a new sample is aspirated.

A radial slot 1230 is provided in each sample bottle recess 1215 within the two azimuthal rows of samples (positions 1-19). Slots 1230 provide a clear field of view of the barcode 1205 of a given sample bottle 1200 with respect to a barcode reader. The barcode reader (not shown) is placed adjacent to the sample carousel 1210 and is positioned with its optical beam directed radially inwards. Barcodes of different sample bottles 1200 are interrogated by rotating the carousel 1210. It is noted that this scheme requires the sample bottle 1200 to be positioned with its barcode label facing radially outward from the carousel 1210. This condition can be ensured by prompting the operator to adjust the orientation of the bottle 1200 if the bar code label cannot be properly read. In an alternative embodiment, a small wheel is brought in contact with the sample bottle when the bottle 1200 is positioned directly in front of the bar code reader. This wheel is rotated by a motor, which in turn causes the bottle to rotation within its cylindrical recess. The bottle is rotated until the bar code can be read by the reader.

Figure 25:
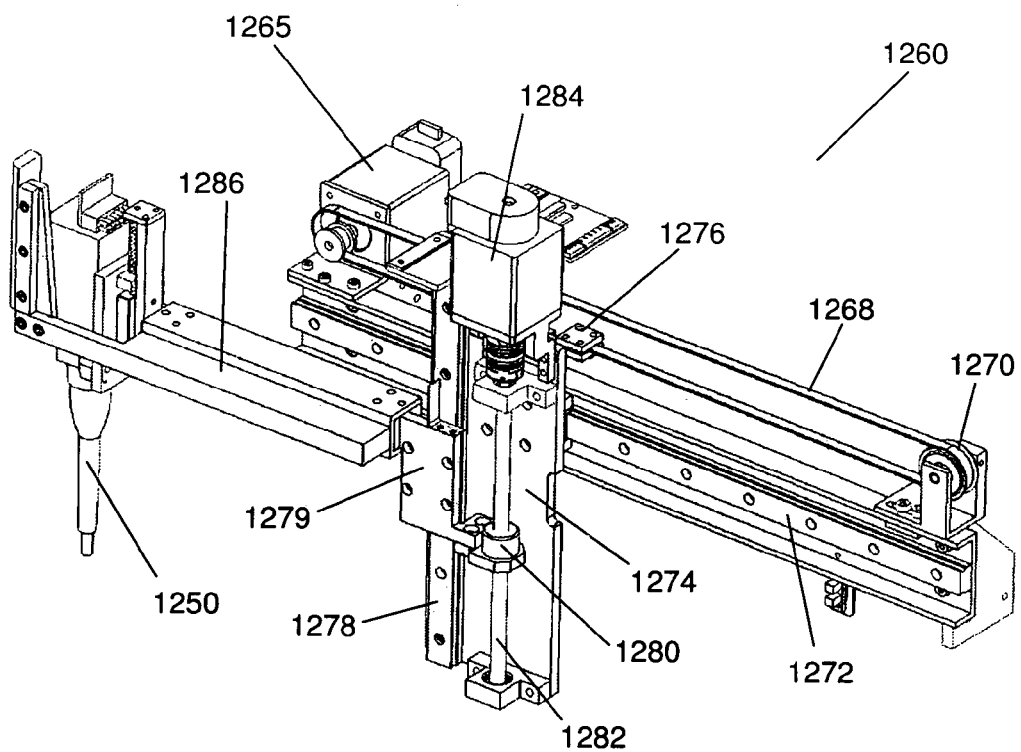
FIG. 25 is a perspective view of the single pipette assembly used to transport samples from the sample dispensing module to a microplate within the analyzer.

Referring to FIG. 25, a precise volume of sample is aspirated from a selected container in the carousel 1210 via a single automated pipette 1250. The pipette 1250 is housed on an assembly 1260 shown in FIG. 25. The assembly 1260 provides the two-dimensional degree of motion required for the pipette 1250 to aspirate the sample, translate it into the main analyzer body, and dispense it into a microplate well. The assembly 1260 is moved in the horizontal direction via a stepper motor 1265 that drives a belt 1268 and pulley 1270 system. A horizontal guide rail 1272 confines the motion of a vertical plate 1274 along the horizontal direction. A clamp 1276 behind the vertical plate couples the horizontal motion of the belt 1268 to the vertical plate 1274. Disposed on the plate is vertical guide rail 1278. The vertical guide rail 1278 precisely confines the motion of a vertical slide 1279. The slide is vertically supported by a nut 1280 that is threaded onto an ACME screw 1282.

A motor 1284 controls the motion of the vertical slide 1278 and hence the pipette 1250. Attached to the vertical slide 1279 is a horizontal standoff 1286 that supports the automated pipette 1250. The standoff 1286 allows the pipette 1250 to traverse the area between the sample dispensing module and transfer zone 425 within the main analyzer system.

Figure 26:
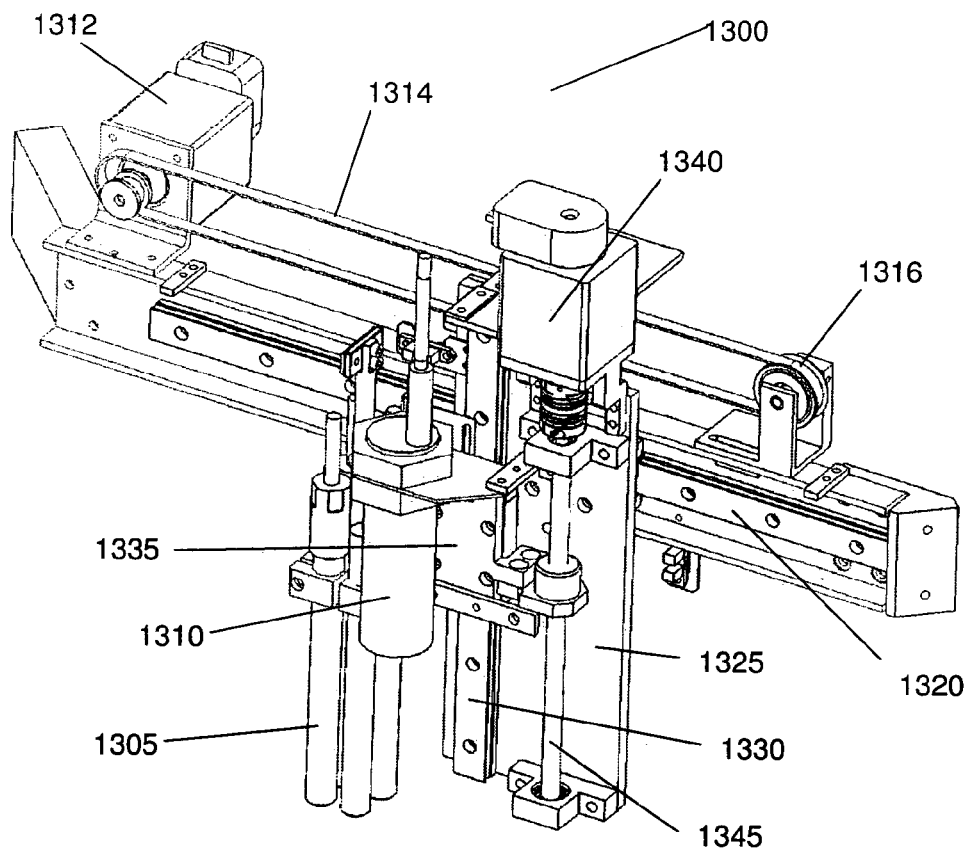
FIG. 26 is a perspective view of the optional probe assembly that is employs ion selective electrodes for additional sample measurements within the sample dispensing module.

A second assembly in the sample dispensing module is the probe assembly 1300, shown in FIG. 26. Like the pipette assembly 1260 described above, the probe assembly 1300 provides two degrees of motion to an electrochemical probes 1305 and an ultrasonic level sensor 1310. The probe assembly 1300 consists of a motor 1312 that drives a belt 1314 and pulley 1316 system. A horizontal guide rail 1320 confines the motion of a vertical plate 1325 along the horizontal direction. The vertical plate 1325 also supports a vertical guide rail 1330. Four ion selective electrode probes are attached to a vertical slide 1335 that is confined by the vertical guide rail 1330. An ultrasonic level sensor 1310 also attached to the vertical slide, provides an accurate measurement of the liquid level displacement in order to submerge the ion selective probes and pipette tip to a chosen depth. A second stepper motor 1340 and ACME screw 1345 system control the vertical motion of the ion selective probes and level sensor 1310. The level sensor 1310 is positioned adjacent to the probes, but at a higher vertical position in order to prevent wetting of the level sensor 1310 while the probes are immersed in a sample. The assembly 1300 therefore allows the placement of electrochemical probes within a chosen sample container via vertical motion. The horizontal motion provides a means of addressing sample locations at different radii on the carousel 1210.

Although the central three recesses 1220 in the carousel 1210 (FIG. 24) preclude barcode scanning, they can be preferably used as locations for storing wash solutions for the ion selective electrodes. If the wash solutions need to be identified, the measurement of sample volume via the liquid level sensor 1310 provides a potential identification means. This can be achieved, for example, by providing the operator with three wash bottles, each having different known volumes that the analyzer can measure and identify. In another embodiment, one or more of the central recesses 1220 can be employed for the housing of a wash container that contains a probe cleaning solution, for example, for the removal of accumulated protein from the ion selective probe membranes. Such a specialty wash solution may produce a clearly recognizable set of signals from the ion selective probes, which can be used to identify the location of the specialty wash solution.

Figure 27:
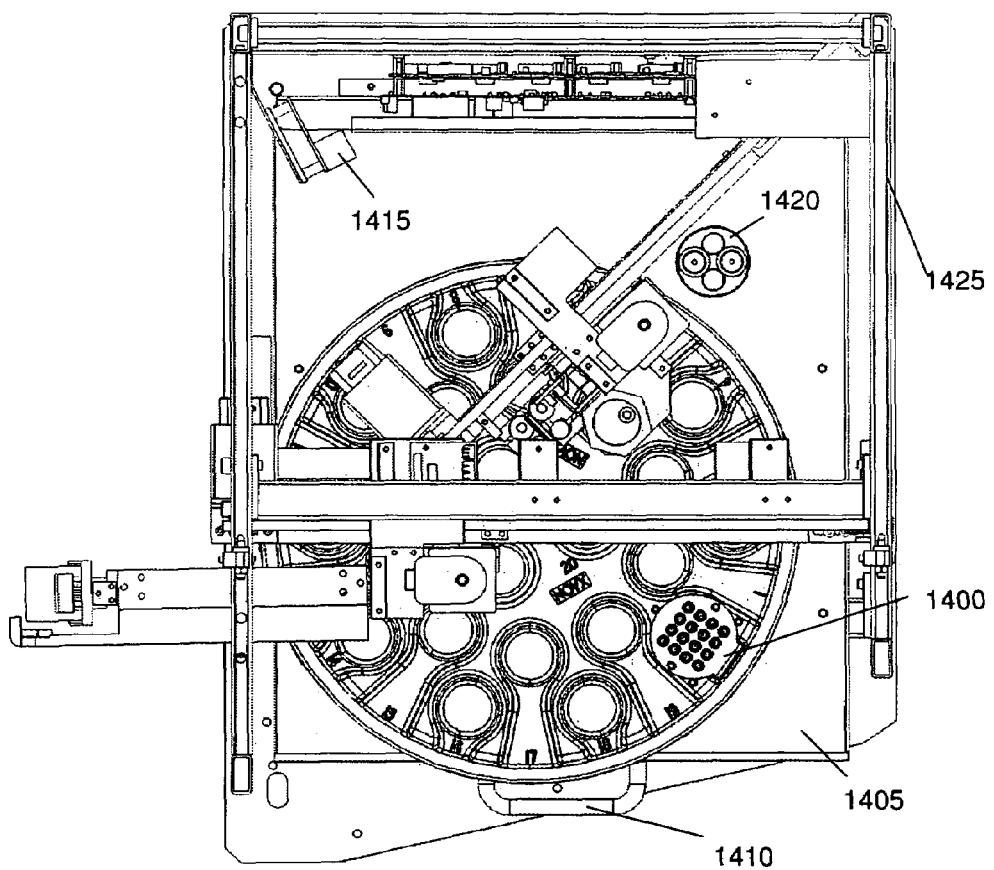
FIG. 27 is a top view of the integrated sample dispensing module, with the pipette assembly shown extended within the main body of the analyzer.
Figure 28:
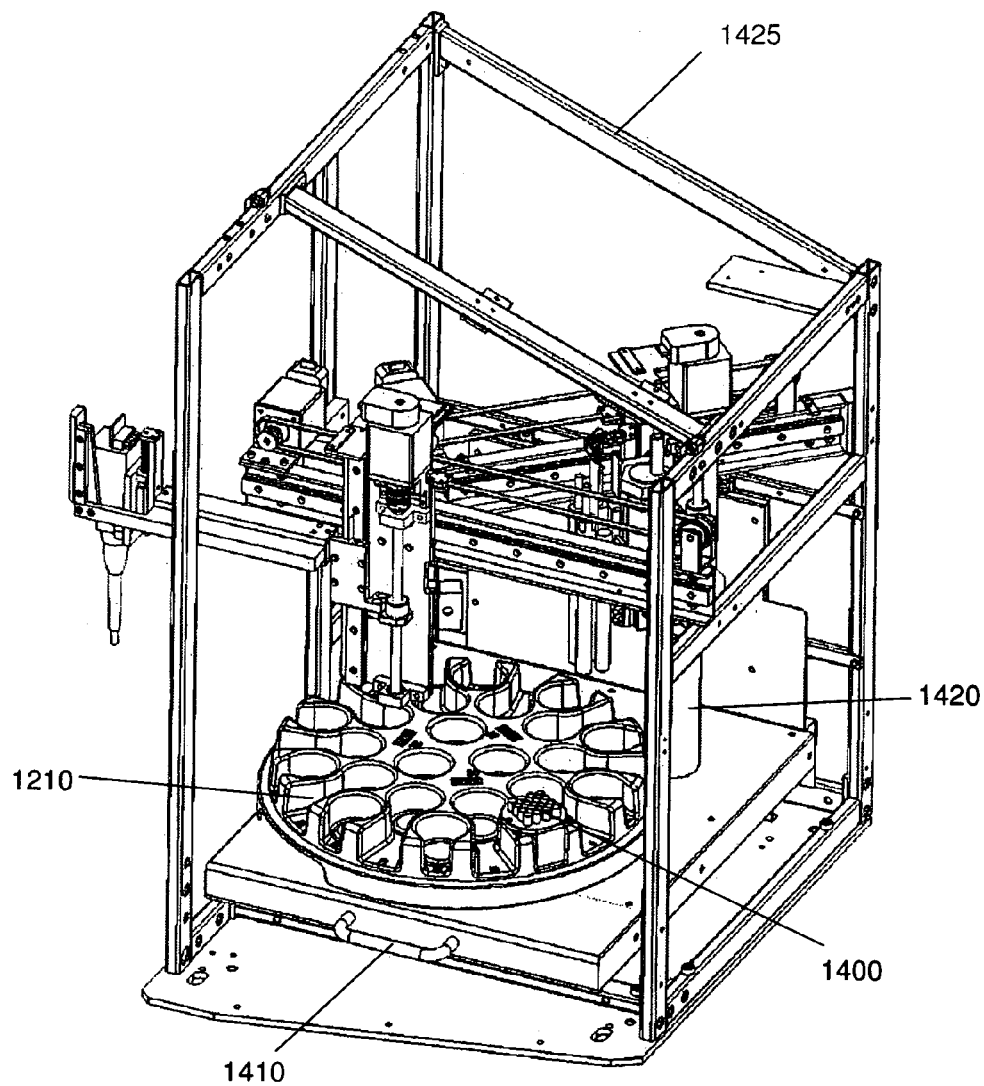
FIG. 28 is a perspective view of the integrated sample dispensing module.

The sample dispensing module, as an integrated subsystem, is shown from above in FIG. 27 and from a diagonal view in FIG. 28. The carousel 1210 loaded with pipette tips 1400 rests on top of a removable tray 1405 with a handle 1410. The handle enables the operator to slide the carousel out of the sample dispensing module housing for the loading of sample bottles. A motor beneath the removable tray drives a pulley system with a timing belt for accurate control of the carousel rotation (not shown). The timing belt connects the motor axle (not shown) to an axle (also not shown) located beneath the center of the carousel. A circular support provides a means of repositioning the motor in order to remove any accrued slack in the timing belt. A bar code reader 1415 interrogates the barcode labels of sample bottles. An additional receptacle 1420 is provided for storage of the electrochemical probes. The sample pipetting assembly 1260 allows the horizontal and vertical translation of the automated pipette from a sample bottle to a microplate within the main body of the analyzer. The probe assembly 1300 translates the electrochemical probes and ultrasonic level sensor at an angle relative to the pipette motion. The probe and level sensor are thus moved in such a manner as to access all sample bottle locations (including the three central positions) in the carousel and the storage receptacle 1420. A metal frame 1425 supports the assembly enclosure (not shown), supports the pipette and probe assemblies, and provides a means of mechanically interfacing the sample dispensing module with the side wall of the main analyzer system.

Figure 29:
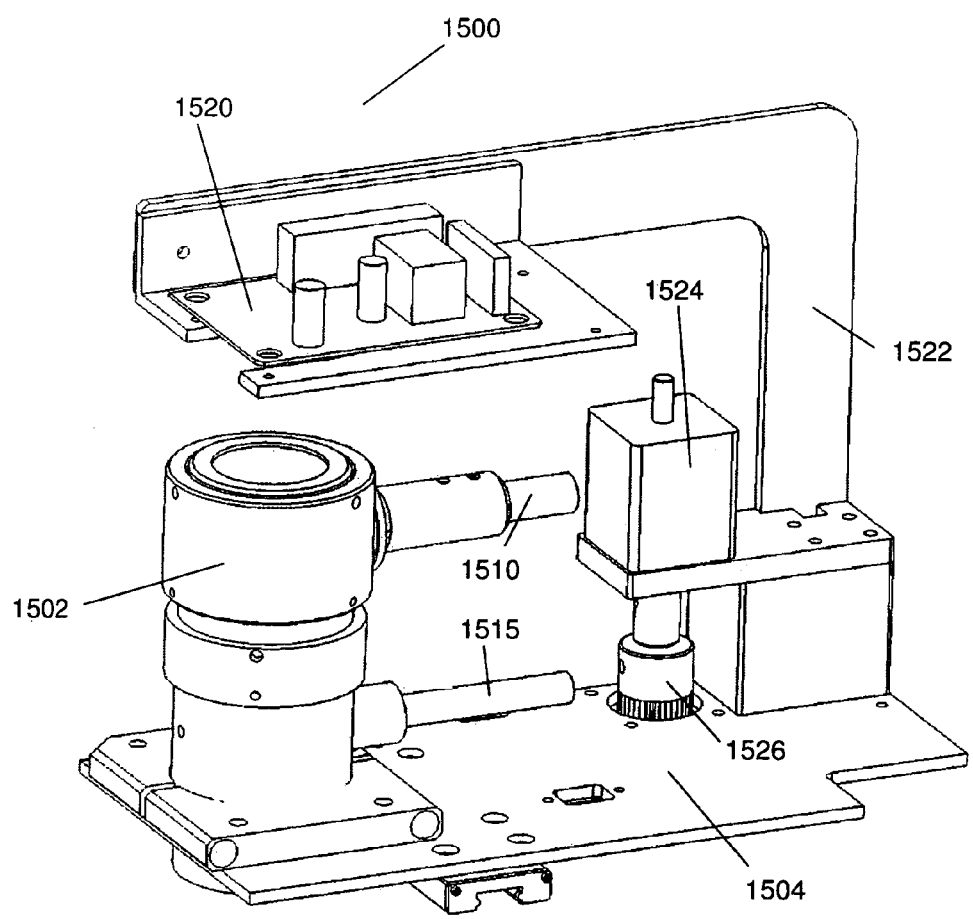
FIG. 29 is a perspective view of the optical head subsystem used to measure absorbance, luminescence or fluorescence within a reaction plate well.

The analyzer incorporates an optical system for the measurement of an optical signal produced or modified by a microwell in a microplate. In a preferred embodiment, a multimode compact optical head is employed to provide measurements of absorbance, fluorescence and luminescence. This preferred optical system 1500 is shown in FIG. 29, where the compact optical head 1502 is pictured on a horizontal platform 1504 that enables the head 1502 to be scanned in a two-dimensional plane directly beneath the optical detection station 430 (see FIG. 6). The details of the compact optical head 1502 are disclosed in co-pending U.S. patent application entitled "OPTICAL SYSTEM", filed on Dec. 7, 2004 with Ser. No. 11/005,325, published as U.S. Patent Publication No. 2006/0119845 which is incorporated herein by reference in its entirety.

The optical head 1502 is fed with two fiber optic bundles 1510 and 1515 (the bundles are truncated in the figure). The upper bundle 1510 delivers a spectrally filtered beam of light for either the excitation of a fluorophore or the measurement of absorbance in a microplate well. This light beam is redirected vertically in the head 1502 and is focused to a small spot within the microplate well. In a preferred embodiment, the beam is gently focused with a numerical aperture of less than 0.20 to a spot size of less than 2 mm in the center of the microwell.

The optical head 1502 also collects light radiated from the microwell, either as fluorescence or luminescence. Within the head 1502, the light is collimated, redirected into the horizontal direction, and refocused onto the emission bundle 1515. The emission bundle 1515 routes the emitted light to a remote location within the analyzer for subsequent filtering and detection. The power of the light beam that is transmitted though the sample is directly measured (with no additional lensing) by a large-area detector mounted beneath a circuit board 1520 that is disposed above the optical head 1502. In a preferred embodiment, the detector is a large-area silicon detector that captures the full power of the transmitted beam. A bracket 1522 supports the absorbance circuit board 1520 and provides sufficient clearance to suspend the detector above a microplate with no mechanical conflicts.

The entire optical subsystem 1500 is scanned in a two-dimensional plane using a combination of two stepper motors and a rack and pinion system. In the figure, only one stepper motor 1524 and one pinion 1526 are shown. The second motor, both racks and the second pinion are placed beneath the horizontal platform 1504. Two guide rails mounted in an orthogonal configuration are employed to accurately confine the linear motion of the assembly. Although other drive systems known in the art may be used to scan the optical head, the dual rack and pinion scheme is preferred for its accuracy and stroke. Factory calibration of the position of the focus within a microplate well ensures that the beam may be placed accurately at the center of all microplate wells for a wide range of microplate types.

In the aforementioned preferred embodiment, the optical head 1502 is scanned beneath a microplate that is held in the optical detection position. This embodiment has the advantage of not disturbing the sample during scanning, which can cause errors due to the motion of the liquid meniscus or the generation and motion of bubbles. The degree of freedom afforded to the head also enables the measurement of a wide variety of microplate form factors and is adaptable to both 96 and 384 well microplates.

As previously discussed, many other embodiments known to those skilled in the art are possible, and may indeed be better suited to some select assays. In particular, if the measurement of fluorescence or luminescence is not required, than it may be preferential to instead incorporate an eight-channel absorbance beam delivery system as known in the prior art. In this scheme, optical power from a single source is split among eight separate legs of a fiber optic bundle and an eight-channel detector array is used to detect each beam simultaneously and independently. The array is scanned across all rows of a 96 well microplate. This system advantageously allows rapid parallel scanning of microplate wells, which for example may be useful in enzyme-based measurements where kinetic measurements are necessary. Although only eight columns are measured at a time, the system is adaptable to a 384 well microplate by providing an additional scanning dimension in the horizontal plane.

Finally, it is also noted that other embodiments in which the microplate is translated relative to a stationary optical head or optical absorbance array are also envisioned as part of the invention. Such schemes simplify the optical path and may remove the requirement for and expense associated with fiber optic bundles by allowing the source and detector systems to be directly integrated with the optical head 1502.

The aforementioned optical head 1502 is used to deliver the incident optical light beam onto the sample within the microplate well and to either measure the absorbed power or collect the emitted fluorescence or luminescence from the contents of the microwell. A separate and remote source and detection subsystem is also disposed within the analyzer. This subsystem 1600 is shown in FIG. 30 with the outer light-tight covering removed, and with all components mounted on a common horizontal base 1605.

The subsystem incorporates a pair of rotating wheels 1610 and 1615 that house a plurality of fixed-wavelength optical filters 1620. Filters are held in place by set screws that butt against the filter holder and can be individually removed by the operator. A photosensor 1622 is used to detect the presence of a notch 1624 in the outer flange of the filter wheel 1615 in order to calibrate the position of the filters relative to a fixed optical axis. In another embodiment, magnetic sensors are used as the sensing element since they advantageously do not generate any stray infrared light.

Figure 30:
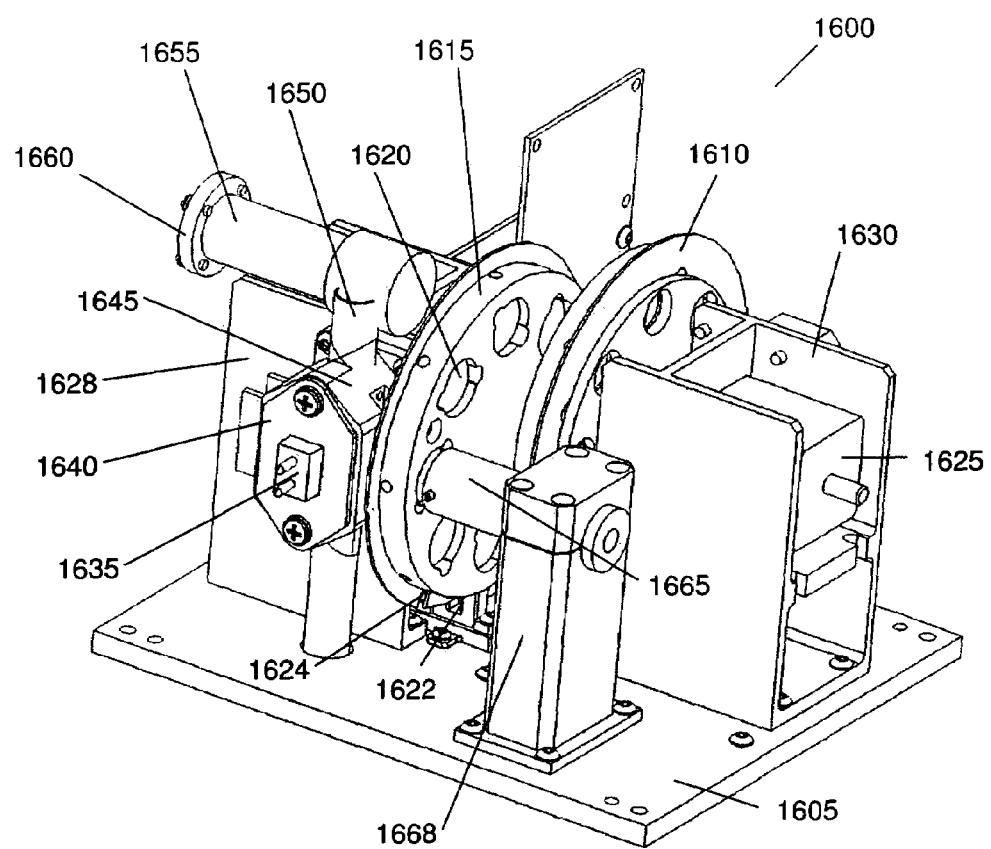
FIG. 30 is a front-left perspective view of the source and detector optical subsystem.

The filter wheels 1610 and 1615 are rotated by stepper motors, one of which 1625 is shown in FIG. 30. Both stepper motors reside in mechanical fixtures 1628 and 1630. A halogen lamp (the socket 1635 is shown in the figure) is held in place by clamping flange 1640. The clamping flange 1640 allows the operator to easily remove a burnt out lamp and install a replacement lamp. In a preferred embodiment, the lamp has a pre-focused base with an accurate diameter and a reference slot that mates precisely with features in the lamp housing 1645, which is itself attached to the motor fixture 1628. This in turn enables the accurate positioning of the lamp filament at the focal point of an aspheric condenser lens that is also placed within the housing 1645.

A vertical tube 1650 connected to a horizontal tube 1655 above the lamp 1635 provides a convective path for airflow around the lamp and also scatters all waste light out of the optical system. A flange 1660 provides a means for suspending the horizontal tube 1655 above the lamp by attaching the tube to the outer wall of the subsystem (not shown). The condenser lens with in the lamp housing 1645 collimates the light emitted by the lamp and directs it along the optical axis passing through the excitation filter wheel 1615. This filter wheel 1615 serves the dual purpose of acting either as a filter for the excitation of a fluorophore within a microplate well or for the generation of a narrowband incident beam for absorbance measurements. After passing through the filter wheel 1615, the collimated and filtered beam encounters a focusing lens housed within a tube 1665. The tube 1665 is supported by a vertical mount 1668. This tube 1665 also supports the ferrule of a fiber optic bundle, onto which the light beam is focused.

The fiber optic bundle is preferably made from a collection of individual fibers that are arranged with a cross-sectional profile that is identical to the image of the filament that is formed on the bundle end face. In a preferred embodiment, the bundle is bifurcated into two legs. One of the legs delivers the optical power to the optical head assembly 1500. The second leg routes optical power back to the source and detector subsystem, where the power is measured in order to provide a means for eliminated deleterious signal variations caused by changes in the lamp power or changes in the position or shape of the filament image. This second source of optical power is henceforth referred to as the reference leg.

Figure 31:
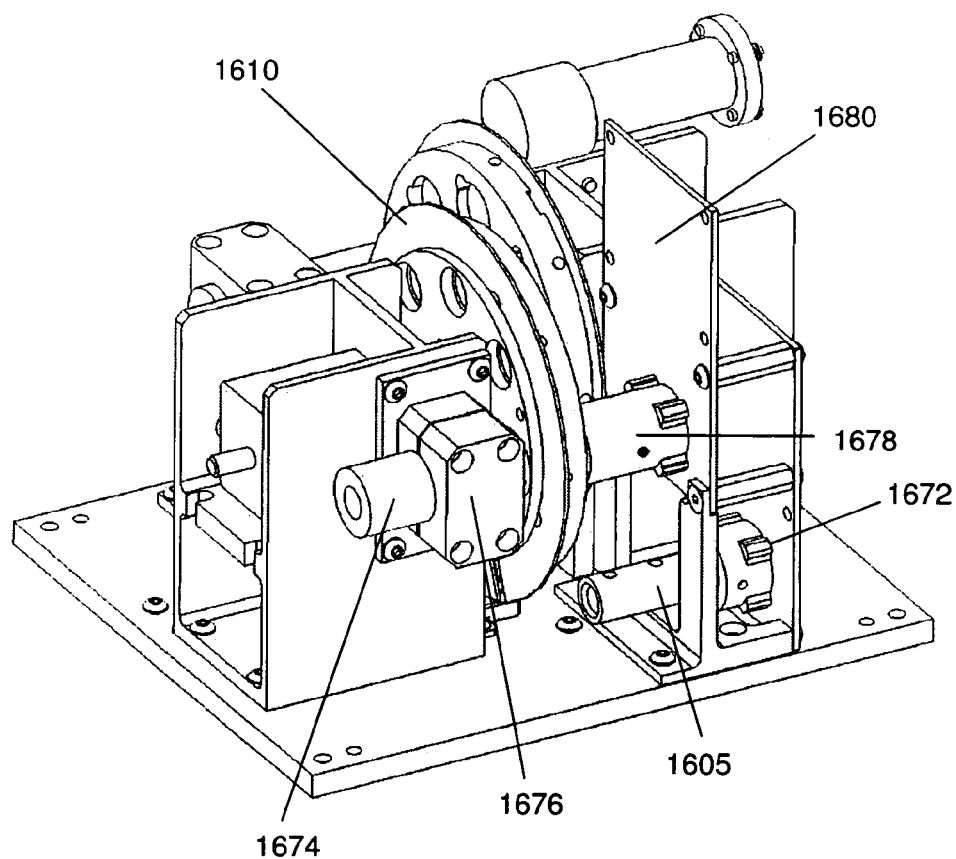
FIG. 31 is a front-right perspective view of the source and detector optical subsystem.

In addition to providing a source of optical power for absorbance measurements or the excitation of a fluorophore, the subsystem also incorporates two detectors for the measurement of optical power from the reference leg and also optical power from a separate fiber optic bundle that delivers collected emission light. These detectors and accompanying components are shown in FIG. 31. The ferrule of the reference leg is held by a tube 1670. The distal end of the ferrule is in close proximity to an optical detector mounted within the tube. The back surface of the optical detector is mounted directly on a printed circuit board 1672. The emission bundle ferrule is also held in a tube 1674 that resides in a clamp 1676. The tube 1674 also includes a lens that collimates the emission light that emerges from the emission bundle. The collimated light passes through a filter in the emission filter wheel 232 before encountering a second tube 1678. This second tube 1678 includes a focusing lens that focuses the filtered emission light onto a detector that is also housed within the tube 1678. The back surface of the detector is also mounted to a second printed circuit board 1680.

Although the emission detector is, in principle, capable of discerning signals of very low optical power, ample provision must be made in order to ensure that stray light emitted by the lamp does not indirectly couple to the detector. Stray lamp light is generated primarily by the excitation filter 1620, where out-of-band light collimated by the condenser lens is rejected. This out-of-band light is reflected back towards to the condenser by the excitation filter, whereupon the lens curvature can scatter a significant fraction of the initial power. This scattered light can then scatter off of multiple components within the source and detector subsystem and eventually couple to the emission detector via the free-space gaps adjacent to the emission filter wheel 1610.

In order block such coupling paths, an opaque light shield, preferably made from sheet metal, is provided that delineates and optically decouples the source section of the subsystem from the detector section. This shield, which is not shown in FIGS. 30 or 31, preferably blocks the entire two-dimensional interface between the source and detector sections by making multiple bends and traveling from the front of the subsystem to the back with no gaps. The light shield therefore enables the emission detector to operate over its full dynamic range with a high signal-to-noise ratio.

The embodiment shown in FIGS. 30 and 31 preferably employs low-noise silicon detectors for the detection of reference or emission light. The subsystem provides a novel, multimode (absorbance, fluorescence and luminescence) optical source and detection system that is easily integrated into the analyzer. However, it will also be readily apparent to those skilled in the art that other embodiments of the optical source and detection assembly are possible without deviating from the scope of the invention. For example, if the emission light is expected to be of very low optical power, a preferred modification to the aforementioned optical subsystem employs a photomultiplier tube for the detection of emission light.

In another embodiment of the invention in which the analyzer does not perform measurements of emitted light but rather only performs multichannel absorbance measurements, the optical system includes only a single filter wheel and a single detector for the reference leg. In this embodiment, there is no need for the opaque light shield since no low-level measurements are made in the source and also because the reference leg optical path is fully contained within the reference tube 1670. Finally, detector noise from external light sources can be eliminated using an optical chopper wheel known in the prior art. The chopper wheel is preferentially located between the filter wheel 1620 and the lens tube 1665 and modulates the optical power delivered to the fiber optic bundle. Detection is achieved using either a narrowband electrical filter or a lock-in detection scheme.

As described above, the preferred embodiment of the optical system employs a scanning optical head that is fed with two fiber optic bundles 1510 and 1515. These bundles 1510 and 1515 each have one end that is fixed in position within the source and detector subsystem. The other end of each bundle, which terminates in the optical head 1500, moves with the head as it is scanned under a microplate held in the optical detection position. It is therefore necessary to provide sufficient slack in each bundle to ensure that the full scanning range is achievable without the application of stress to the bundles. In particular, it is necessary to ensure that the minimum bend radius of the bundles is not compromised, which can lead to mechanical failure and breakage of optical fibers.

In a preferred embodiment, this requirement is satisfied by providing a large circular or elliptical loop within the bundle. As the optical head scans toward its most distant position, the loop tightens and provides the needed slack to the bundle. Mechanical fixtures at selected positions within the analyzer confine the region of space accessible to the bundles and ensure that the minimum bend radius is not exceeded. This scheme can be successfully applied to both the excitation (or absorbance) bundle and the emission bundle. Since the reference leg has both its origin and termination in fixed positions, it can be routed in a fixed path within the analyzer and does not require a looping scheme.

Figure 32:
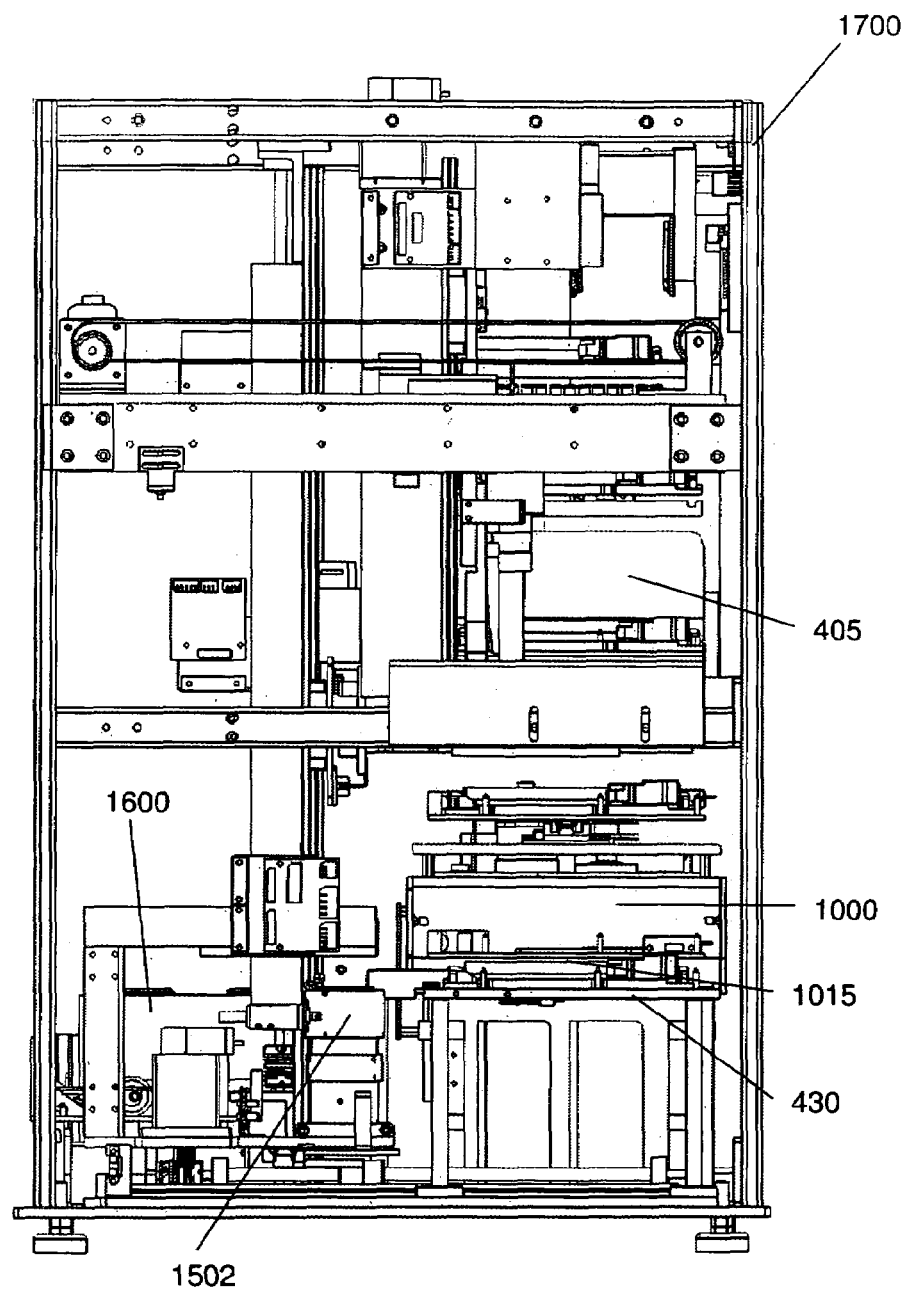
FIG. 32 is a front perspective view of the main body of the analyzer with all integrated subsystems.
Figure 33:
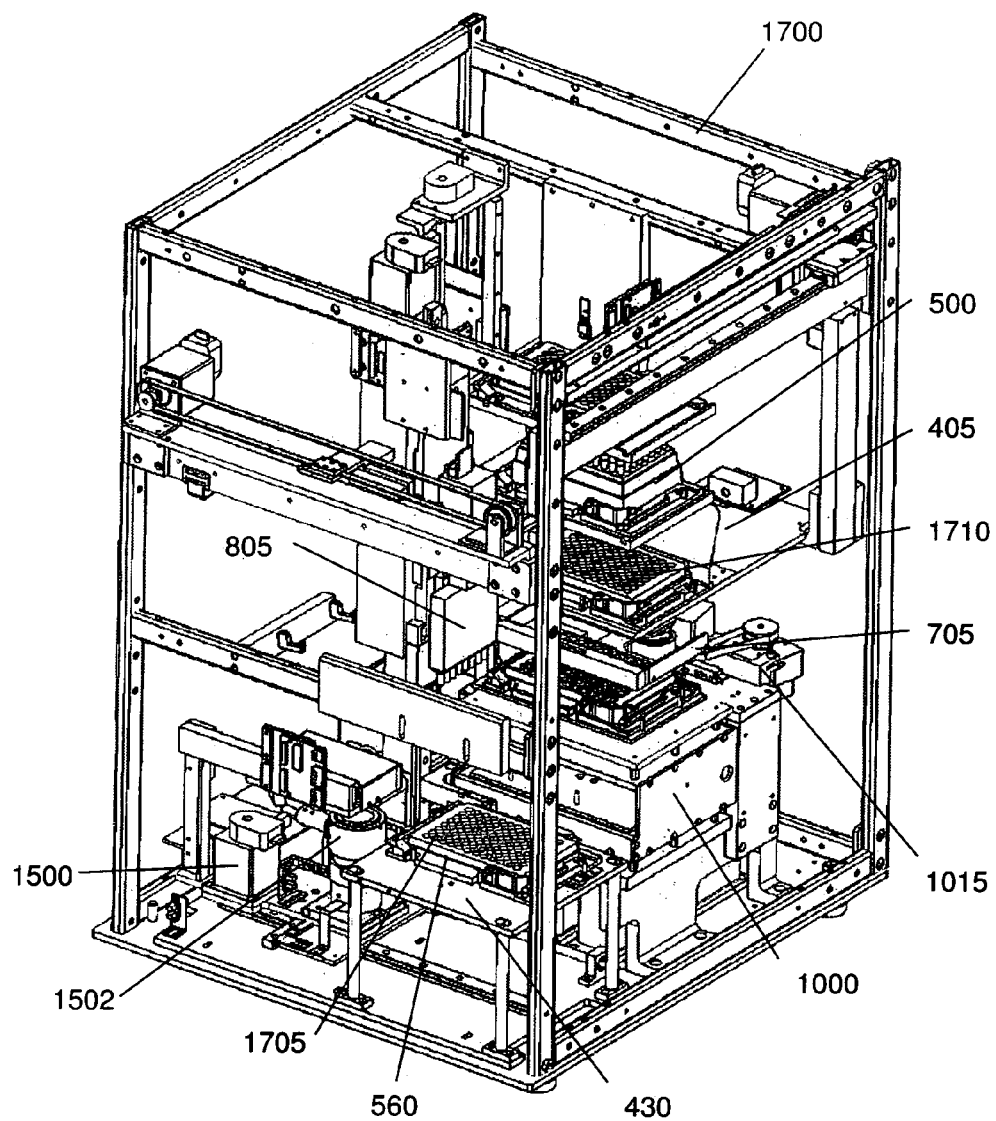
FIG. 33 is a top-right perspective view of the main body of the analyzer with all integrated subsystems.

A schematic of the main analyzer system with all aforementioned subsystems (except for the sample dispensing module) is provided in FIGS. 32 and 33 (both figures show an identical state of the analyzer). The subsystems are arranged within an outer frame 1700. Each subsystem is modular and can be independently added to, or removed from, the analyzer, enabling the analyzer to be assembled in a configuration that provides only those subsystems that are needed by a given customer. A microplate 1705, supported upon a microplate carrier tray 560, is shown in the optical detection position 430. Behind the optical detection position lies the incubator 1000 and secondary vortexer 1015. In FIG. 33, a reagent microplate 1710 can be seen placed upon the loading arm 405. A pipette tip box 500 and an additional reagent microplate are shown placed upon the two upper park positions.

In FIG. 33, the transport arms 705 of the carrier tray transport assembly are shown below the loading arm 405. The multichannel pipettor 805 is shown in its retracted position. As previously described, the multichannel pipettor can be moved in and out of the transfer zone (the open area above the optical detection position) for the transfer of liquids to and from microplates. FIG. 32 clearly illustrates the optical head 1502 and related assembly 1500 in its retracted position (the fiber optic bundles are not shown). The optical source and detector assembly 1600 is visible enclosed in a light-tight box behind the optical head assembly.

The analyzer incorporates a processor and control system to automate the various robotic functions required to perform assay batch protocols and to manage the multiple internal control systems. Results generated at the conclusion of a batch protocol run are provided to the operator in a number of possible formats, including the LCD, a thermal printer, or a network connection through a standard protocol such as a serial RS232, USB, ethernet or WiFi. In a preferred embodiment, the analyzer seamlessly interfaces to an internet-based laboratory management system that analyzes, reports and archives the sample data in a secure fashion.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An automated analyzer for performing chemical, biochemical or biological assays in a microplate format, comprising;

a plurality of discrete carrier trays for holding and transporting microplates and other assay consumables, where said microplates and assay consumables have a uniquely identifiable label, and where microplates with microwells containing a reagent or standard are initially provided in a sealed format;

means of presenting said carrier trays to an operator for the purpose of loading or unloading said microplates and other assay consumables;

a plurality of carrier tray supports within said analyzer for holding said carrier trays in particular locations;

a carrier tray transport means for transporting said carrier trays as required within said analyzer;

a sample housing for holding one or more sample containers, where each sample container has a uniquely identifiable machine readable label;

reading means for reading a machine readable label;

piercing means for piercing said sealed microwells for allowing access to the reagents or standards within the microwells;

a liquid dispensing system for transferring a sample to said microwell and for transferring one or more of said reagent or standard to one microplate from another microplate;

agitation means for agitating one or more microplates;

a thermal incubator for thermally incubating contents of said microwells of one or more microplates;

an optical detection station including an optical detection system for measuring an assay signal from one or more microwells;

a user interface enabling interaction between the analyzer and an operator;

microprocessor control means including firmware pre-programmed with one more batch protocols, wherein said batch protocols describe all steps required for the automation of one or more assays performed on one or more samples; and a means for field-updating said firmware for the purpose of adding, removing or modifying batch protocols.

2. The analyzer according to claim 1 wherein said uniquely identifiable labels on said microplates and assay consumables are machine readable.

3. The analyzer according to claim 2 wherein said machine readable labels are any one of one-dimensional barcodes, two-dimensional barcodes, text, and radio-frequency identification tags.

4. The analyzer according to claim 2 wherein separate reading means are provided for reading said machine readable labels on said microplates and consumable and said machine readable labels on said sample containers.

5. The analyzer according to claim 2 wherein said machine readable labels on said microplates include any one or more of microplate type, microplate vendor, expiry date, production date, lot or batch number, serial number, reagent or standard identity and location, and reagent or standard concentration.

6. The analyzer according to claim 2 wherein said machine readable labels on said assay consumables includes any one or more of the following: consumable type, consumable vendor and consumable format.

7. The analyzer according to claim 2 wherein said batch protocols further contain information regarding the type of microplates and consumables required to perform said one or more assays, wherein a correct identity of microplates and consumables loaded by an operator can be verified via said machine readable labels on said microplates and consumables.

8. The analyzer according to claim 1 further including an internal wash station for the washing of one or more microplates.

9. The analyzer according to claim 8 further including an internal wash buffer storage reservoir.

10. The analyzer according to claim 1 wherein said means of presenting said carrier trays to an operator for the purpose of loading or unloading said microplates and other assay consumables is a motorized loading arm that extends through a door in said analyzer.

11. The analyzer according to claim 1 wherein said means of presenting said carrier trays to an operator for the purpose of loading or unloading said microplates and other assay consumables is a door in said analyzer providing access to said carrier trays residing on said carrier tray supports within said analyzer.

12. The analyzer according to claim 1 wherein one or more of said carrier tray supports are included in said analyzer for the purpose of storing said carrier trays.

13. The analyzer according to claim 12 wherein said one or more carrier tray supports are vertically grouped in a magazine structure.

14. The analyzer according to claim 12 wherein said one or more carrier tray supports are placed within said analyzer without mutual shadowing in the vertical direction for the purpose of enabling the direct transfer of liquids from between microplates housed in said carrier trays held by said one or more carrier tray supports.

15. The analyzer according to claim 1 wherein said carrier tray supports further include a proximity sensor for detecting the presence or absence of a carrier tray.

16. The analyzer according to claim 1 wherein one or more carrier trays have a thermally conductive base, where an internal area of said thermally conductive base is raised relative to an outer area of said base for the purpose of positioning an upper surface of said internal area of said base in close proximity to one or more microwells of a microplate loaded onto said carrier plate.

17. The analyzer according to claim 16 wherein said internal area of said base contains an array of through holes, wherein an axis of each through hole is substantially parallel to an axis of a microwell located above said through hole.

18. The analyzer according to claim 17 wherein each through hole has a diameter that is sufficiently large to pass a substantial amount of light directed through or emitted from the microwell positioned above said through hole, wherein said diameter of said through hole is sufficiently narrow to provide sufficient thermal exchange between said base and said microwell positioned above said through hole.

19. The analyzer according to claim 16 wherein said one or more carrier trays are configured to perform passive thermal incubation for a microplate during the automation of an assay.

20. The analyzer according to claim 1 wherein said carrier tray transport system includes a pair of transport arms, said transport arms being connected at one end by a support bar, and wherein said transport arms further include one or more protrusions for the purpose of engaging with recesses in a carrier tray for the purpose of transporting said carrier tray.

21. The analyzer according to claim 1 wherein said sample housing includes means for moving said sample containers relative to said reading means to enable the reading of said machine readable labels on said sample containers.

22. The analyzer according to claim 1 wherein said sample housing includes means for moving said sample containers relative to said liquid dispensing means to enable the aspiration of samples from said sample containers.

23. The analyzer according to claim 1 wherein said machine readable labels are any one of one-dimensional barcodes, two-dimensional barcodes, text, and radio-frequency identification tags.

24. The analyzer according to claim 1 wherein said reading means for reading a machine readable label is an optical barcode reader.

25. The analyzer according to claim 1 wherein said reading means for reading a machine readable label detects radio-frequency identification tags.

26. The analyzer according to claim 1 wherein said piercing means is a piercing tool used externally by an operator.

27. The analyzer according to claim 1 wherein said piercing means is a piercing tool residing within said analyzer.

28. The analyzer according to claim 27 wherein said piercing means is permanently attached to a translating subsystem within said analyzer.

29. The analyzer according to claim 27 wherein said piercing means is attached to a translating subsystem within said analyzer in a removable fashion.

30. The analyzer according to claim 1 wherein said liquid dispensing system includes a single-channel electronic pipetting system.

31. The analyzer according to claim 1 wherein said liquid dispensing system includes a multi-channel electronic pipetting system.

32. The analyzer according to claim 1 wherein said liquid dispensing system includes an electronic pipetting system utilizing a pipetting means including any one of air displacement, peristaltic, positive displacement and syringe pumping.

33. The analyzer according to claim 1 wherein said liquid dispensing system employs disposable pipette tips.

34. The analyzer according to claim 1 wherein said agitation means comprises two orthogonal translation stages that can be motorized to move in an arbitrary profile.

35. The analyzer according to claim 1 wherein said agitation means is an orbital vortexer with a fixed orbital radius.

36. The analyzer according to claim 1 further including a second agitation means for agitating one or more microplates.

37. The analyzer according to claim 1 wherein said optical detection system measures any one or more of absorbance, fluorescence, luminescence, chemiluminescence, electroluminescence, time-resolved fluorescence, and fluorescence polarization.

38. The analyzer according to claim 1 wherein said optical detection system comprises a scanning optical head that moves relative to the microwells of a microplate.

39. The analyzer according to claim 1 wherein said optical detection system comprises a stationary optical head, and wherein said microplate carrier supporting said microplate moves relative to said stationary optical head.

40. The analyzer according to claim 1 wherein said optical system comprises a multi-channel optical head providing a simultaneous measurement of absorbance for a plurality of neighbouring microwells.

41. The analyzer according to claim 1 wherein said optical detection system and said thermal incubator are combined in a single system wherein said optical detection is performed within said thermal incubator.

42. The analyzer according to claim 1 wherein said thermal incubator is a passive thermal incubator wherein said microwells are maintained at a substantially equal temperature.

43. The analyzer according to claim 1 wherein said machine readable label on a sample container includes a list of assays to be performed on said sample.

44. The analyzer according to claim 1 wherein said machine readable label on a sample container identifies a batch protocol to be performed on said sample.

45. The analyzer according to claim 1 wherein said user interface is a touchscreen liquid crystal display integrated into said analyzer.

46. The analyzer according to claim 1 wherein said user interface includes means for restricting an operator from programming said firmware.

47. The analyzer according to claim 1 wherein said firmware is remotely updated over an internet connection.

48. The analyzer according to claim 1 wherein a result of an automated assay is obtained remotely over an internet connection.

49. The apparatus according to claim 1 wherein said batch protocols include sample batch protocols for the automation of one or more assays on one or more samples and wherein said batch protocols further include, for each sample batch protocol, a corresponding calibration protocol whereby assays are performed with standards having known analyte concentrations for the purpose of obtaining a dose-response curve for said one or more assays.

50. The analyzer according to claim 1 wherein said assay consumables include disposable pipette tips housed in a box having a physical footprint and size compatible with one or more of said carrier trays.

51. The analyzer according to claim 1 wherein said sample housing includes one or more ion selective probes for the measurement of ionic concentrations in a sample and a means for automating the immersion of said probes into said samples.

* * * * *